(12) United States Patent
Brar et al.

(10) Patent No.: US 7,468,052 B2
(45) Date of Patent: Dec. 23, 2008

(54) TREATMENT OF STENOTIC REGIONS

(76) Inventors: Balbir S. Brar, 26261 Glen Canyon, Laguna Hills, CA (US) 92653; Harvinder Sahota, 3861 Wisteria St., Seal Beach, CA (US) 90740

(*) Notice: Subject to any disclaimer, the term of this patent is extended or adjusted under 35 U.S.C. 154(b) by 0 days.

(21) Appl. No.: 11/757,960

(22) Filed: Jun. 4, 2007

(65) Prior Publication Data

US 2007/0233173 A1    Oct. 4, 2007

Related U.S. Application Data

(63) Continuation of application No. 10/444,234, filed on May 23, 2003, now Pat. No. 7,226,473.

(51) Int. Cl.
*A61M 29/00* (2006.01)
*A61M 37/00* (2006.01)

(52) U.S. Cl. ............... 604/96.01; 623/921; 604/103.1; 604/103.11

(58) Field of Classification Search ........ 623/1.11–1.42; 604/96.01, 103.1, 103.11
See application file for complete search history.

(56) References Cited

U.S. PATENT DOCUMENTS

| | | | |
|---|---|---|---|
| 4,468,224 A | 8/1984 | Enzmann et al. | |
| 4,545,390 A | 10/1985 | Leary | |
| 4,581,017 A | 4/1986 | Sahota | |
| 4,655,771 A | 4/1987 | Wallsten | |
| 4,735,665 A | 4/1988 | Miyauchi et al. | |
| 4,771,778 A * | 9/1988 | Mar | 606/192 |
| 4,950,227 A | 8/1990 | Savin et al. | |
| 5,242,399 A | 9/1993 | Lau et al. | |
| 5,242,451 A | 9/1993 | Harada et al. | |
| 5,300,085 A | 4/1994 | Yock | |
| 5,346,505 A | 9/1994 | Leopold | |
| 5,354,279 A | 10/1994 | Hofling | |

(Continued)

FOREIGN PATENT DOCUMENTS

EP    0 707 837 A1    4/1996

(Continued)

OTHER PUBLICATIONS

Schetky, L.M. 1979. Shape-Memory Alloys, Scientific American, 241(5):74-82.

(Continued)

*Primary Examiner*—Suzette J Gherbi
(74) *Attorney, Agent, or Firm*—Knobbe, Martens, Olson & Bear, LLP

(57) ABSTRACT

An improved method and devices for preventing restenosis are provided. The method may include delivering a stent configured to contain a stenosis to a body vessel. The method may also include using atherectomy at the site prior to stent delivery. In one embodiment, the stent has a proximal end, a distal end, and a center portion arranged such that the diameters of the proximal and distal ends are greater than the diameter of the center portion. In one embodiment, the atherectomy device includes a housing to prevent injury to the unaffected areas of the body vessels but the cutter is extendible beyond the housing. In one embodiment, the stent may be impregnated with at least one drug after stent deployment.

2 Claims, 23 Drawing Sheets

U.S. PATENT DOCUMENTS

| | | | |
|---|---|---|---|
| 5,421,955 A | 6/1995 | Lau et al. |
| 5,445,646 A | 8/1995 | Euteneuer et al. |
| 5,458,613 A | 10/1995 | Gharibadeh et al. |
| 5,516,781 A | 5/1996 | Gregory et al. |
| 5,551,954 A | 9/1996 | Buscemi et al. |
| 5,591,227 A | 1/1997 | Dinh et al. |
| 5,741,333 A | 4/1998 | Frid |
| 5,755,769 A | 5/1998 | Richard et al. |
| 5,759,192 A | 6/1998 | Saunders |
| 5,769,883 A | 6/1998 | Buscemi et al. |
| 5,836,966 A | 11/1998 | St. Germain |
| 5,837,313 A | 11/1998 | Ding et al. |
| 5,891,108 A | 4/1999 | Leone et al. |
| 5,893,839 A | 4/1999 | Johnson |
| 5,954,706 A | 9/1999 | Sahatjian |
| 5,972,027 A | 10/1999 | Johnson |
| 6,004,346 A | 12/1999 | Wolff et al. |
| 6,010,530 A | 1/2000 | Goicoechea |
| 6,042,875 A | 3/2000 | Ding et al. |
| 6,071,305 A | 6/2000 | Brown et al. |
| 6,077,295 A | 6/2000 | Limon et al. |
| 6,124,523 A | 9/2000 | Banas et al. |
| 6,129,705 A | 10/2000 | Grantz |
| 6,203,536 B1 | 3/2001 | Berg et al. |
| 6,206,914 B1 | 3/2001 | Soykan et al. |
| 6,249,952 B1 | 6/2001 | Ding |
| 6,253,443 B1 | 7/2001 | Johnson |
| 6,254,632 B1 | 7/2001 | Wu et al. |
| 6,273,913 B1 | 8/2001 | Wright et al. |
| 6,283,947 B1 | 9/2001 | Mirzaee |
| 6,293,959 B1 | 9/2001 | Miller et al. |
| 6,306,422 B1 | 10/2001 | Batich et al. |
| 6,316,018 B1 | 11/2001 | Ding et al. |
| 6,325,820 B1 | 12/2001 | Khosravi et al. |
| 6,451,373 B1 | 9/2002 | Hossainy et al. |
| 6,458,076 B1 | 10/2002 | Pruitt |
| 6,652,568 B1 * | 11/2003 | Becker et al. ............... 623/1.11 |
| 6,702,850 B1 | 3/2004 | Byun et al. |
| 6,712,842 B1 | 3/2004 | Gifford et al. |
| 6,833,002 B2 | 12/2004 | Stack et al. |
| 7,226,473 B2 * | 6/2007 | Brar et al. .................. 623/1.11 |
| 2001/0029660 A1 | 10/2001 | Johnson |
| 2003/0018376 A1 | 1/2003 | Solar et al. |
| 2003/0023141 A1 | 1/2003 | Stelzer et al. |
| 2003/0028078 A1 | 2/2003 | Glukhovsky |
| 2003/0040712 A1 | 2/2003 | Ray et al. |
| 2003/0055318 A1 | 3/2003 | Vierra et al. |
| 2003/0060877 A1 | 3/2003 | Falotico et al. |
| 2004/0001841 A1 | 1/2004 | Nagavarapu et al. |
| 2004/0015228 A1 | 1/2004 | Lombardi et al. |
| 2004/0024416 A1 | 2/2004 | Yodfat et al. |
| 2004/0127973 A1 | 7/2004 | Mangiardi et al. |
| 2004/0143322 A1 | 7/2004 | Litvack et al. |
| 2005/0182481 A1 | 8/2005 | Schlick et al. |
| 2007/0014804 A1 | 1/2007 | Burkhard |
| 2007/0254852 A1 | 11/2007 | Matin et al. |

FOREIGN PATENT DOCUMENTS

| | | |
|---|---|---|
| WO | WO 99/16386 | 4/1999 |
| WO | WO 99/16500 | 4/1999 |
| WO | WO 00/12147 | 3/2000 |
| WO | WO 01/01957 A1 | 1/2001 |
| WO | WO 03/009773 | 2/2003 |

OTHER PUBLICATIONS

International Search Report and Written Opinion dated Jan. 18, 2005; PCT/US2004/015903, filed May 5, 2004.

* cited by examiner

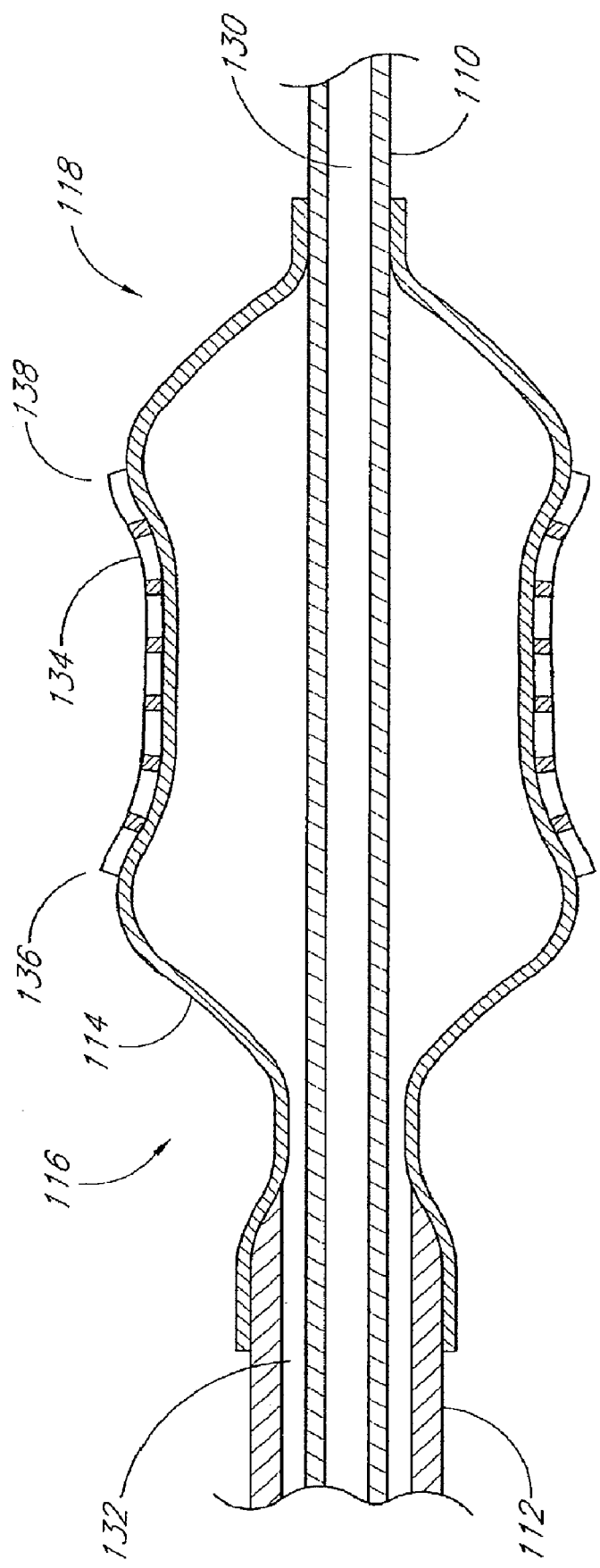

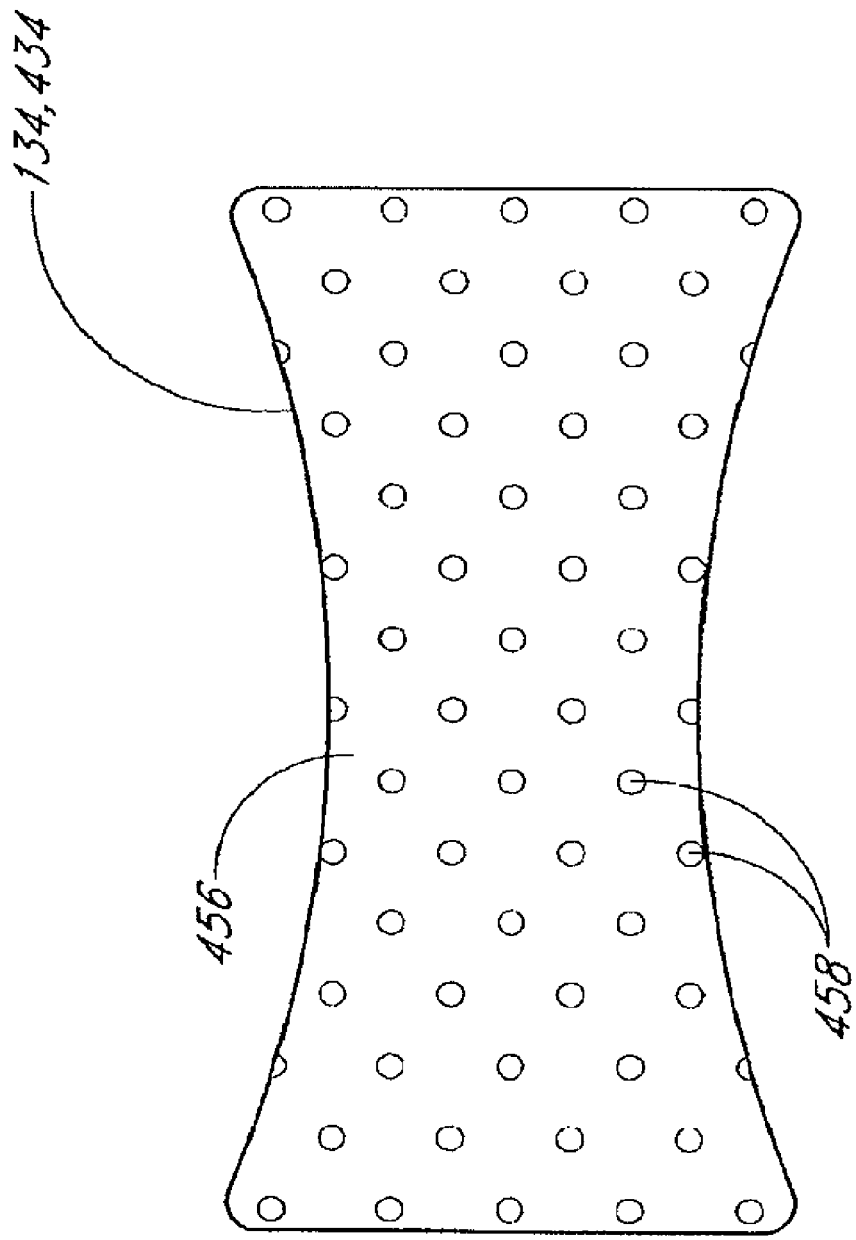

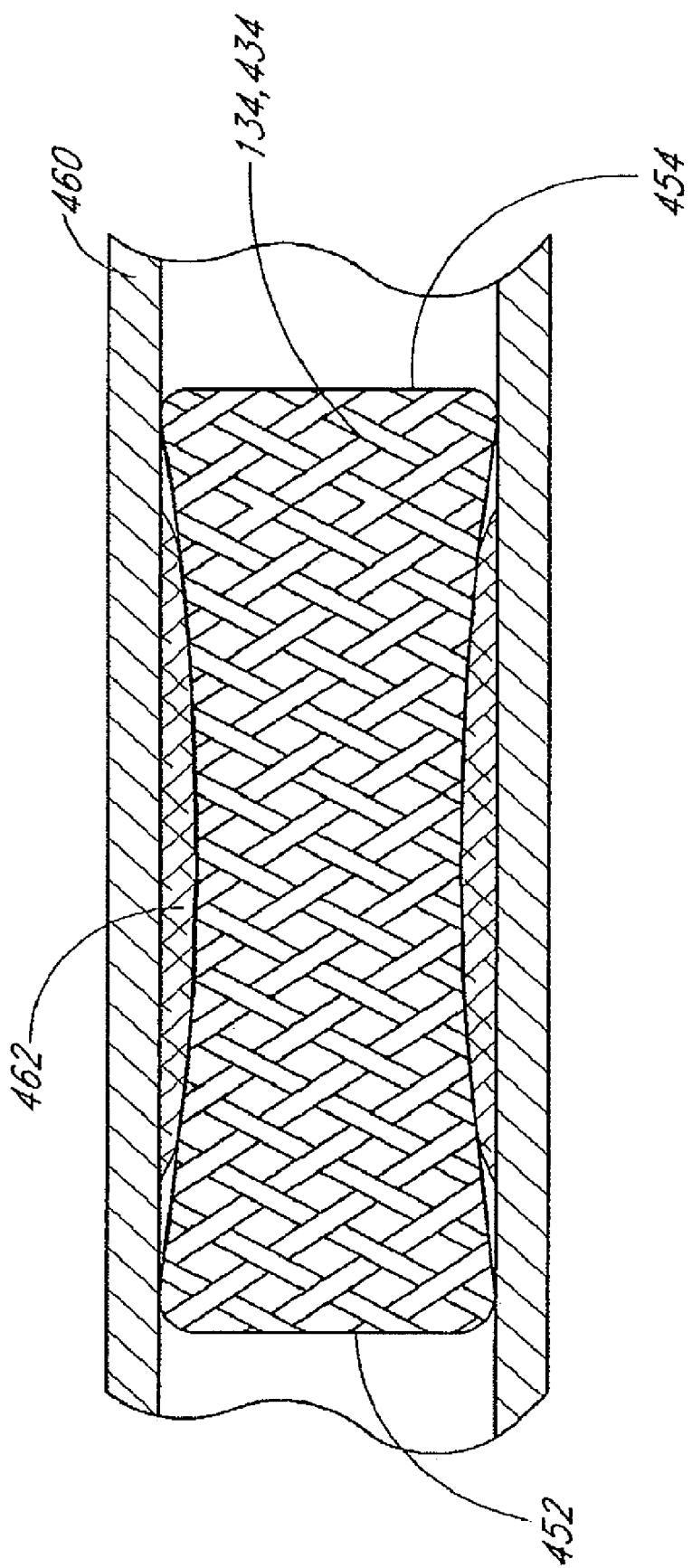

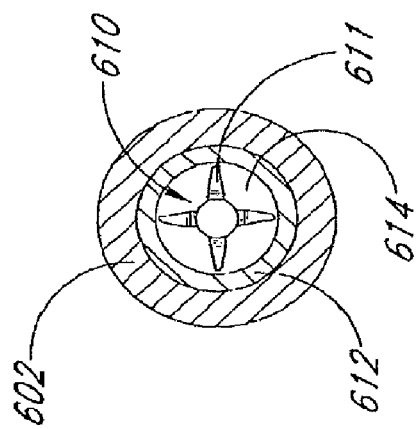
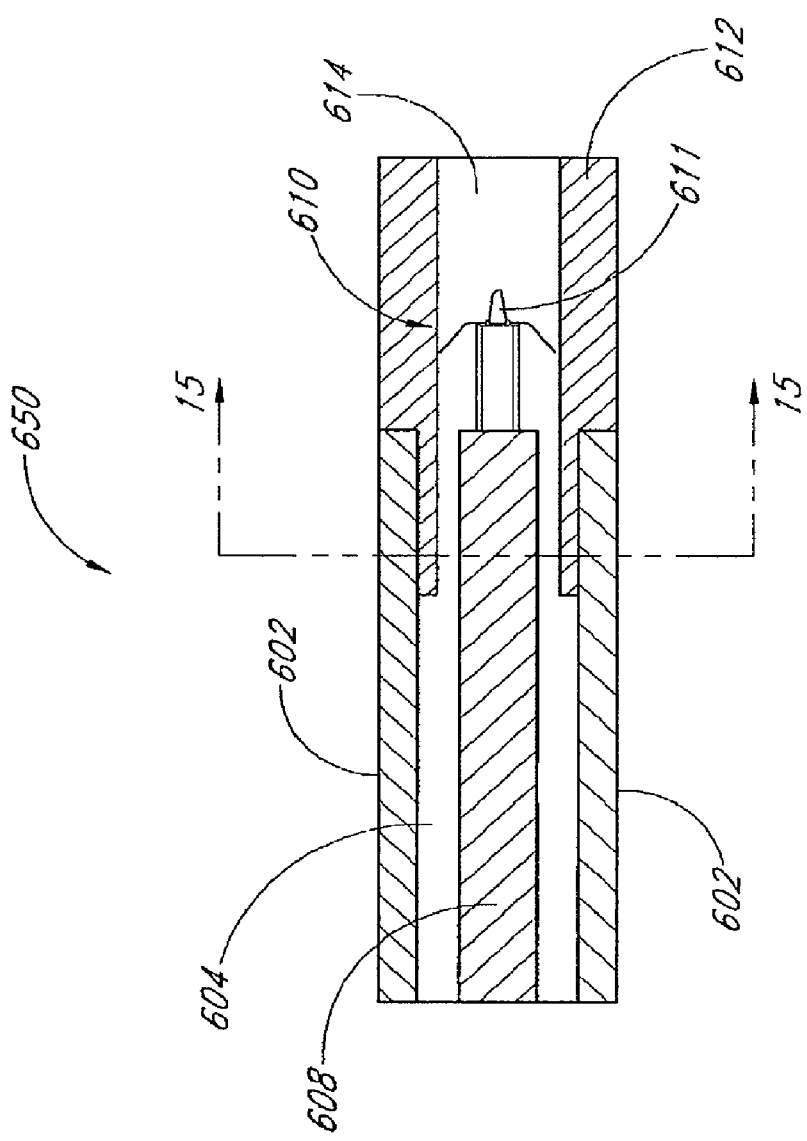

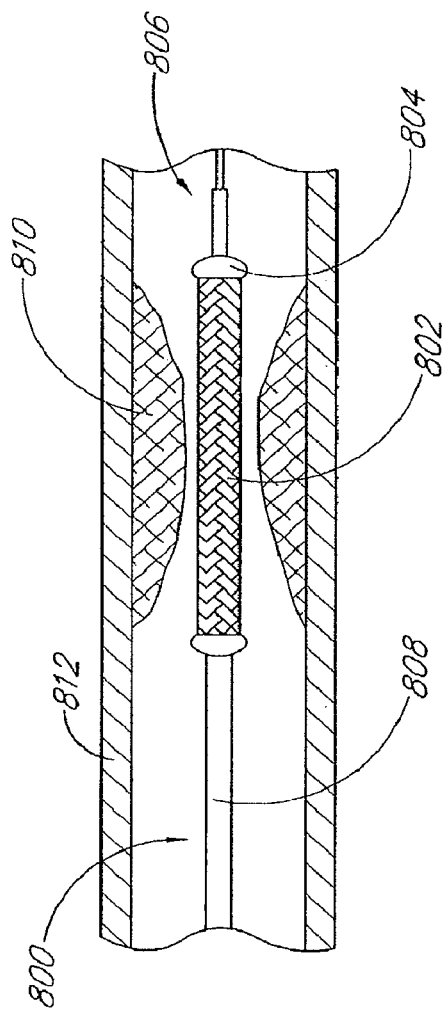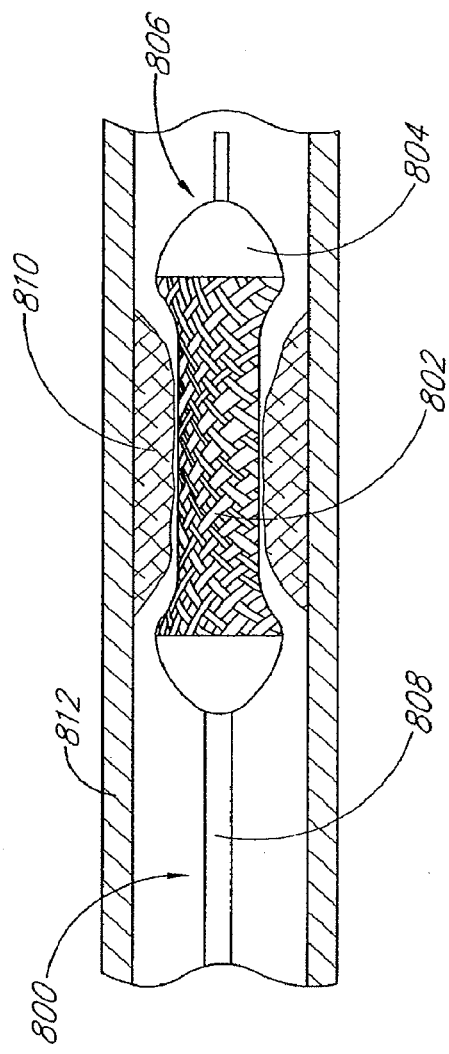

TREATMENT OF STENOTIC REGIONS

This application is a continuation of U.S. application Ser. No. 10/444,234, filed on May 23, 2003, and entitled "TREATMENT OF STENOTIC REGIONS", which is incorporated herein by reference in its entirety.

BACKGROUND OF THE INVENTION

1. Field of the Invention

The present invention relates to medical devices and, in particular, to methods and devices of preventing restenosis.

2. Description of the Related Art

Many causes of restenosis in angioplasty have been theorized among health care professionals. Many diseases cause body lumens to undergo stenosis or a narrowing of a canal within the body. The resulting reduced blood flow can permanently damage tissue and organs. Stenotic regions that limit or obstruct coronary blood flow are a major cause of ischemic heart disease related mortality.

The therapeutic alternatives generally used for treatment of stenosis involve intervention (alone or in combination of therapeutic agents) to remove the blockage, replacement of the blocked segment with a new segment of artery, or the use of catheter-mounted devices such as a balloon catheter to dilate the artery. The dilation of an artery with a balloon catheter is called percutaneous transluminal angioplasty (PTA). A stent may also be delivered, as known in the art.

Often angioplasty permanently opens previously occluded blood vessels; however, restenosis thrombosis, or vessel collapse may occur following angioplasty. A major difficulty with PTA is the problem of post-angioplasty closure of the vessel, both immediately after PTA (acute reocclusion) and in the long term (restenosis).

Re-narrowing (restenosis) of an artery after angioplasty occurs in 10-50% of patients undergoing this procedure and subsequently requires either further angioplasty or other procedures. Restenosis (chronic reclosure) after angioplasty is a more gradual process than acute reocclusion: 30% of patients with subtotal lesions and 50% of patients with chronic total lesions will go on to restenosis after angioplasty. Because 30-50% of patients undergoing PTCA will experience restenosis, restenosis has limited the success of PTCA as a therapeutic approach to coronary artery disease.

Recently, intravascular stents have been the focus of substantial attention as a means of preventing acute reclosure after PTA. Most stents are delivered to the desired implantation site percutaneously via a catheter or similar transluminal device. Once at the treatment site, the compressed stent is expanded to fit within or expand the lumen of the passageway. Stents are typically either self-expanding or are expanded by inflating a balloon that is positioned inside the compressed stent at the end of the catheter. Intravascular stents are often deployed after coronary angioplasty procedures to reduce complications, such as the collapse of arterial lining, associated with the procedure.

However, stents do not entirely reduce the occurrence of thrombotic abrupt closure due to clotting; stents with rough surfaces exposed to blood flow may actually increase thrombosis, and restenosis may still occur because tissue may grow through and around the stent and the lattice of the stent.

SUMMARY OF THE INVENTION

In accordance with one embodiment of the present invention, improved methods and devices for inhibiting and preventing restenosis are provided.

In one embodiment, a stent has a tubular body having a proximal end, a distal end, and a center portion, wherein the diameter of the proximal end and the diameter of the distal end are greater than the diameter of the center portion, such that the stent contains a stenosis.

In one embodiment, the distal end and proximal end each extend about 1-6 mm beyond the stenosis. In another embodiment, the distal end and proximal end each extend about 5 mm beyond the stenosis. In another embodiment, the distal end and proximal end each extend at least 1 mm beyond the stenosis. The stent may be self-expanding or balloon expandable. In one embodiment, the stent includes at least one drug. In one embodiment, the stent includes a plurality of drugs. The drug may include a time-released drug. In one embodiment, the diameter of the proximal end is equal to the diameter of the distal end. In another embodiment, the diameter of the proximal end is greater than the diameter of the distal end. In another embodiment, the diameter of the distal end is greater than the diameter of the proximal end.

In one embodiment, an atherectomy device having an axially movable cutting element and a tubular housing surrounding the cutting element to protect undamaged vessels from the cutting element is provided.

In one embodiment, a catheter placement device having a guidewire, a bent tubular element, wherein the tubular element is adapted to be delivered over the guidewire and a balloon for stabilizing the directional catheter at a bifurcated vessel is provided.

In one embodiment, a method of inhibiting restenosis is provided. The method includes performing atherectomy at a vessel site, and delivering a stent to the site. The stent may have a tubular body having a proximal end, a center portion, and a distal end, arranged such that proximal end and distal end have a larger diameter than the center portion, such that the stent contains a stenosis.

In one embodiment, a method of inhibiting restenosis is provided. The method includes delivering a stent to a treatment site, and impregnating the stent with at least one drug at the treatment site. The stent may be impregnated about 3-6 months after the stent is delivered to the treatment site. In one embodiment, the delivering a stent and impregnating the stent are performed with a substantial time between the two steps.

In one embodiment, a drug impregnation catheter having an elongate tubular body having a proximal end and a distal end, and a balloon attached to the distal end of the tubular body, wherein the balloon comprises a coating comprising at least one therapeutic agent is provided.

The systems and methods have several features, no single one of which is solely responsible for its desirable attributes. Without limiting the scope as expressed by the claims that follow, its more prominent features will now be discussed briefly. After considering this discussion, and particularly after reading the section entitled "Detailed Description of the Preferred Embodiments" one will understand how the features of the system and methods provide several advantages over traditional systems and methods.

BRIEF DESCRIPTION OF THE DRAWINGS

FIG. 3A is a detailed longitudinal-sectional view of the distal end of the catheter and expanded stent of FIG. 1.

FIG. 8A is an alternative view of a stent in accordance with an embodiment of the present invention.

FIG. 14 is a detailed longitudinal-sectional side view of the atherectomy device of FIG. 13.

FIG. 15 is a detailed cross-sectional end view of the atherectomy device of FIG. 13.

FIGS. 19-24 are schematic views of the methods in accordance with one embodiment.

DETAILED DESCRIPTION OF THE PREFERRED EMBODIMENTS

The devices are described with reference to the accompanying figures, wherein like numerals refer to like elements. The terminology used in the description is not intended to be interpreted in any limited or restrictive manner simply because it is being utilized in conjunction with a detailed description of certain specific embodiments. Furthermore, embodiments may include several novel features, no single one of which is solely responsible for its desirable attributes or which is essential to practicing the inventions herein described. The words in the claims are presented to have the customary and ordinary meanings.

Methods and devices for inhibiting restenosis are disclosed. A stent delivery catheter system in which a stent is delivered intraluminally into a body lumen, such as a coronary artery, carotid artery, renal arteries, peripheral arteries and veins, and the like is also disclosed. The catheter system is also useful in the brain, the urethral system and the vascular system.

Stent Delivery Device

Figure 1:
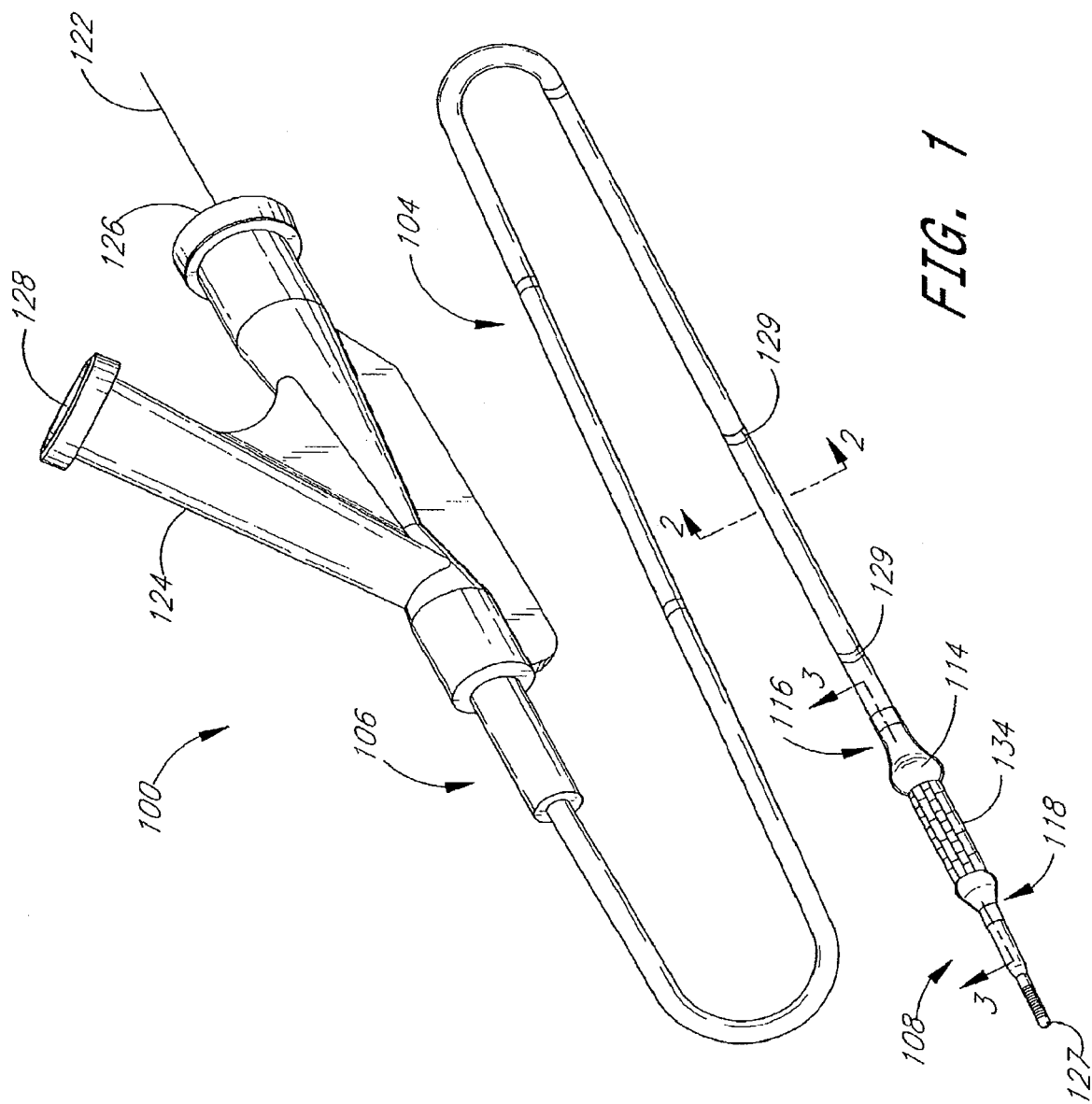
FIG. 1 is a perspective view showing a catheter having a stent of the present invention.

A stent delivery catheter 100 is shown in FIG. 1. Delivery catheter 100 preferably includes an elongate, flexible tubular shaft 104, having a proximal end 106 and a distal end 108. The shaft 104 defines one or more passages or lumens extending through the shaft.

Catheter 100 preferably comprises a balloon 114, having a proximal end 116 and a distal end 118. Elongate shaft 104 preferably includes a guide wire 122, extending from distal end 116 through proximal end 106 of shaft 104, providing rigidity to device 100. Catheter 100 also includes a manifold 124. Manifold 124 preferably includes a guide wire port 126 and an inflation port 128. Catheter 100 may also include radiopaque markers 129 to view the location of catheter 100 within the patient's body lumen. Catheter 100 may also include a soft, flexible distal tip 127. Such catheters are known.

Figure 2:
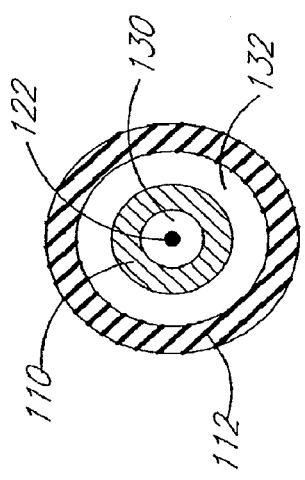
FIG. 2 is a cross-sectional view showing the catheter of FIG. 1 through line 2-2.

FIG. 2 shows a cross-sectional view of the elongate shaft 104, showing inner sleeve 110 and outer sleeve 112. The inner sleeve 110 defines a guide wire lumen 130, while the inflation lumen 132 is defined by the annular space between the inner sleeve 110 and outer sleeve 112. The guide wire lumen 130 is adapted to receive an elongate guide wire 122 in a sliding fashion through proximal guide wire port 126 in catheter manifold 124. The particular position and arrangement of lumens is merely exemplary.

Preferably, inflation lumen 132 is coupled to the balloon 114 to selectively inflate it with the inflating fluid. The inflation lumen 132 provides fluid communication between the interior of the balloon 114 at the distal end of the inflation lumen 132 and the inflation port 128 located at manifold 124.

The inflation lumen 132 may also be adapted to hook up to a vacuum, to eliminate air bubbles. Alternatively, a separate lumen may be provided for connection with the vacuum. Vacuum lumen would also be in communication with the internal cavity of balloon 114.

The catheter shaft 104 may have various configurations other than the coaxial design shown in the drawings, including a single extruded multi-lumen tube defining any suitable number of colinear, parallel or radially aligned lumens.

Figure 3:
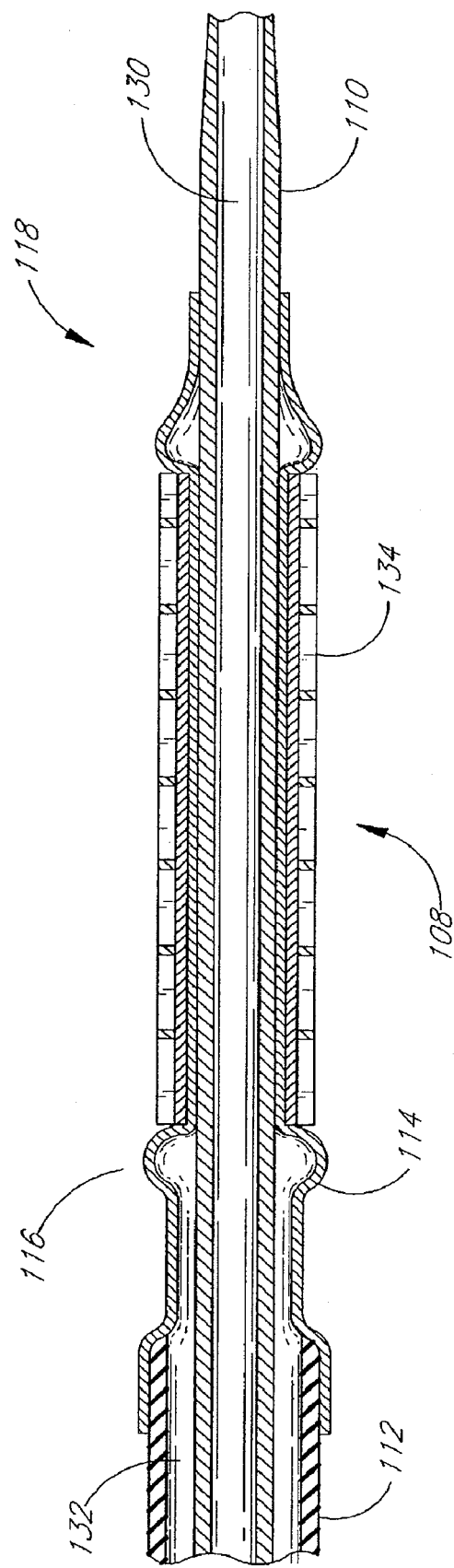
FIG. 3 is a detailed longitudinal-sectional view of the distal end of the catheter and stent of FIG. 1 through line 3-3.

The stent 134 depicted in FIG. 1 is preferably removably carried by the distal end 108 of elongate shaft 104. Stent 134 has an initial diameter at which it is inserted into a body lumen, and an expanded final diameter. Stent 134, as shown in FIGS. 1, 3 and 3A, is a balloon-expandable slotted metal tube (usually but not limited to stainless steel or the like), which when expanded within the lumen, provides structural support to the arterial wall. Stent 134 comprises a tubular structure. Although stent 134 is illustratively shown in the configuration 100 of FIG. 1, the stent 100 may be of virtually any configuration so long as stent 100 meets the needs of the treatment procedures. Configurations, such as helices, coils, braids, expandable tube stents, roving wire stents, and wire mesh stents or the like may be utilized depending on the application for the device.

The balloon 114 may comprise a substantially inelastic, compliant material. Many balloon configurations are known. The balloon 114 is formed from any suitable biocompatible material. The balloon 114 is preferably removably attached to the catheter shaft 104 by affixing its distal end to the inner sleeve 110, and its proximal end to the outer sleeve 112. The balloon 114 thereby communicates with the annular inflation lumen 132 between the inner sleeve 110 and outer sleeve 112. The balloon 114 may alternatively be attached to the shaft 104 in any way that allows it to be inflated with fluid from the inflation lumen 132.

The catheter manifold 124 provides a maneuvering handle for the health care professional, as well as an inflation port 128 and a guide wire port 126. Either or both the inflation port 128 or the guide wire port 126 may have a coupling, accompanied by a luer-lock fitting for connecting an inflation lumen to a source of pressurized fluid in a conventional manner. The manifold 124 may also include an injection port for allowing radiopaque contrast fluid to be injected through the outer sleeve and around the catheter shaft, thus illuminating the delivery device on a fluoroscope. The proximal manifold 124 is preferably injection molded of any suitable material. A precision gasket may also be provided, which seals securely around the device, prohibiting fluid loss. Many other catheter configurations are also known.

FIG. 3A illustrates stent 134 in an expanded configuration being deployed by the balloon 114. Stent 134 is expanded by inflating balloon 114. The balloon is preferably configured to expand stent 134 into the desired configuration. As shown in FIG. 3A, the balloon 114 is preferably configured to have a larger diameter at the proximal end 116 and distal end 138 of the stent, while having a relatively smaller diameter at the center of the stent.

The size of stent 134 varies, depending on the particular treatment and access site. The overall length, diameter and wall thickness may vary based on the treatment. In a preferred embodiment, stent 134 has an inflated length between about 1 and 10 cm, preferably about 3-5 cm. In a preferred embodiment, stent 134 has an inflated diameter between about 0.1 and 1.5 cm. However, stents of any suitable dimension for the application may be used.

Figure 4:
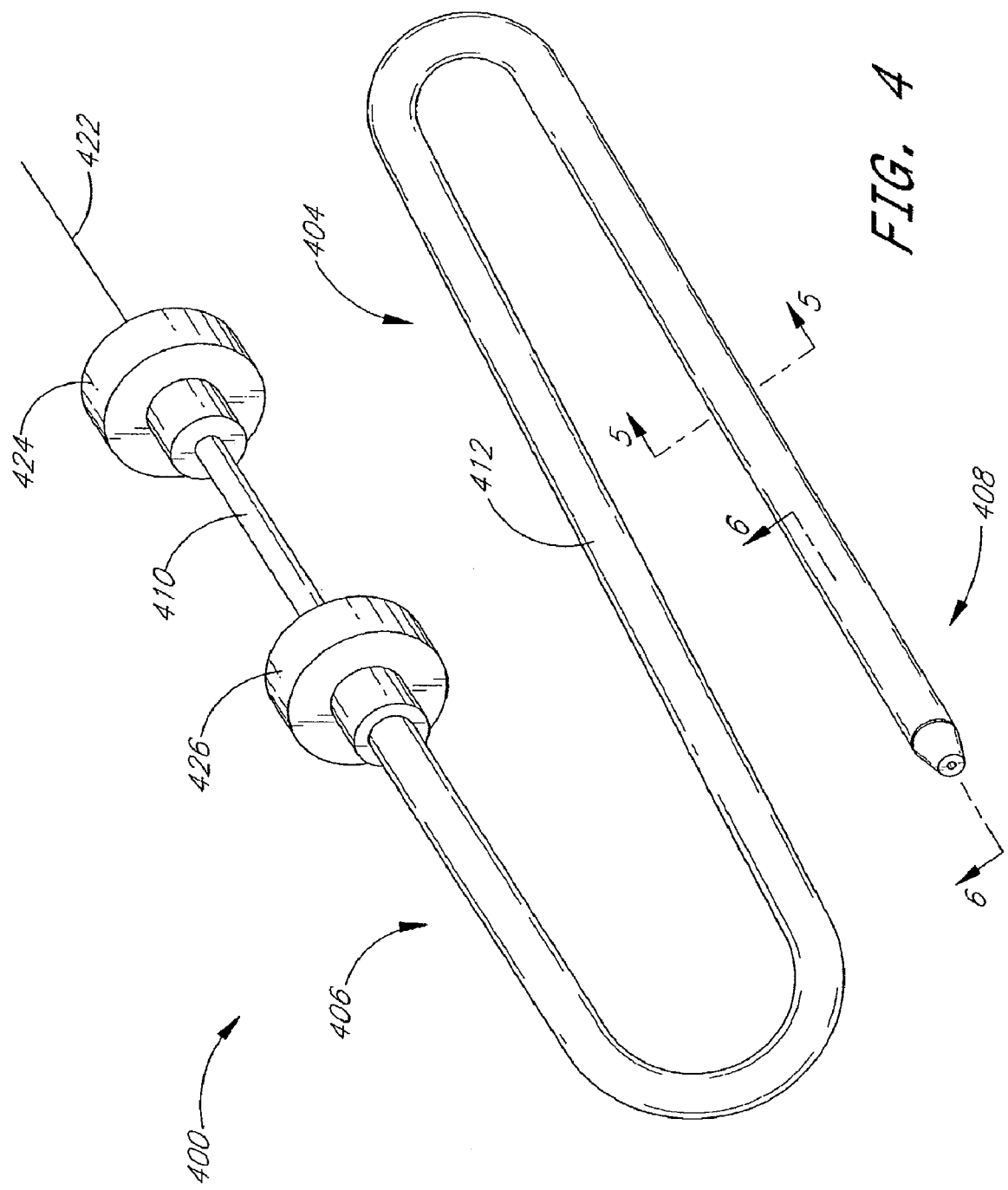
FIG. 4 is a perspective view showing an alternative embodiment of a catheter having a stent of the present invention.

One alternative embodiment of a stent delivery catheter is depicted in FIG. 4 for delivery of self-expanding stents. Delivery catheter 400 preferably includes an elongate, flexible tubular shaft 404, having a proximal end 406 and a distal end 408. The shaft 404 defines one or more passages or lumens extending through the shaft.

Figure 5:
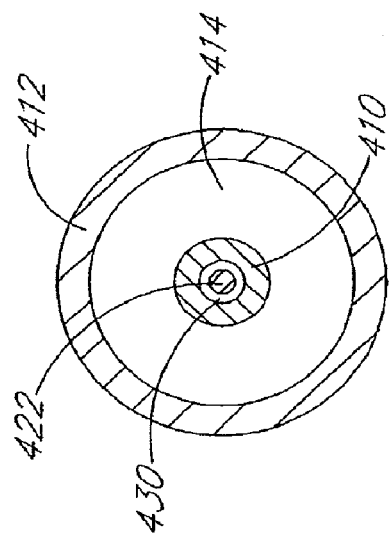
FIG. 5 is a cross-sectional view showing the catheter of FIG. 4 through line 5-5.

An inner member 410 and an outer member 412 are preferably arranged in coaxial alignment, as shown in FIG. 5. Member 412 forms an inner lumen 414. Inner member 410 is slidably positioned within inner lumen 414 of outer member 412 and relative axial movement between the two members is provided by inner member control handle 424 and outer member control handle 426 (see FIG. 4).

Figure 6:
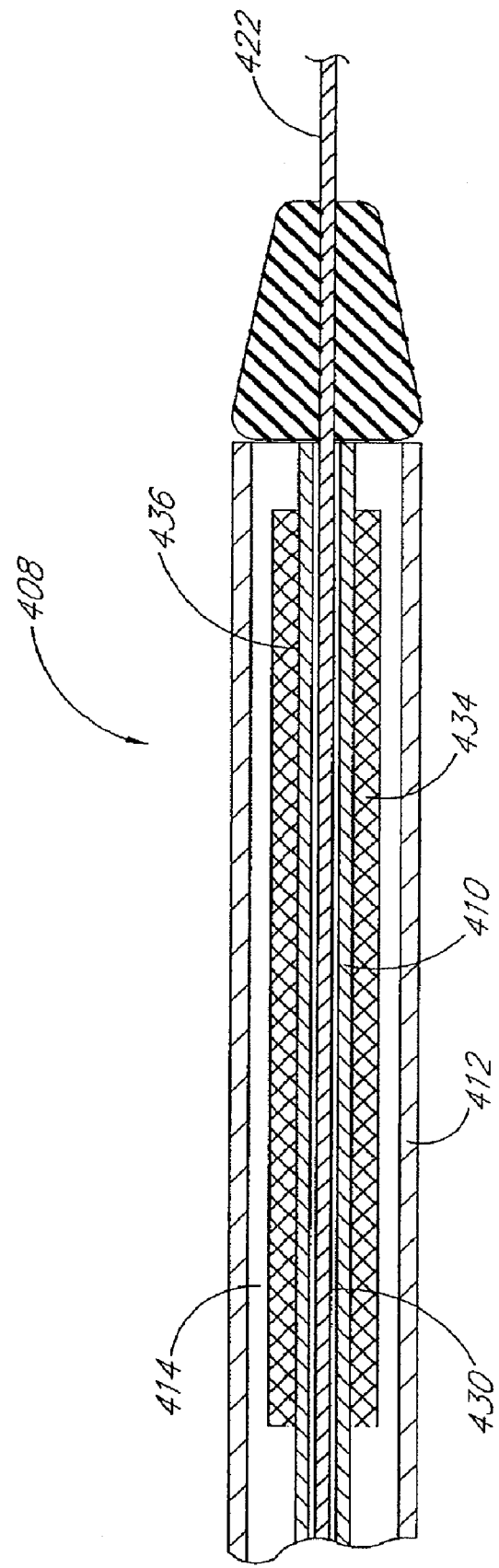
FIG. 6 is a detailed longitudinal-sectional view of the distal end of the catheter and stent of FIG. 4 through line 6-6.

A self-expanding stent 434, as shown in FIG. 6 is mounted within the distal end 408 of catheter 400. Stent 434 comprises a tubular structure, having an inner lumen 436. Self-expanding stent 434 can take virtually any configuration self-explanding stent. Configurations, such as helices, coils, braids, expandable tube stents, roving wire stents, and wire mesh stents or the like may be utilized depending on the application for the device.

The self-expanding stent 434 is inserted in outer member inner lumen 414 and positioned at the outer member distal end. In those instances where self-expanding stent 434 is made from a material that is biased outwardly, stent 434 will be compressed and inserted into inner lumen 414. Thereafter, the distal end of inner member 410 is positioned within stent inner lumen 436 so that the outer surface of inner member 410 can come into contact with the stent inner lumen 436.

Inner member 410 is preferably made from a polymeric material that either is soft by design, or will become soft when heat is applied. The intent is to removably attach self-expanding stent 434 on the outer surface of inner member 410. Inner member 410 will partially fill the open lattice structure of stent 434 so that the stent 434 cannot move in an axial direction along the outer surface of inner member 410.

Self-expanding stent 434 is mounted on outer surface at the distal end of inner member 410. Due to the coaxial arrangement between inner member 410 and outer member 412, the inner lumen 414 of outer member 412 covers self-expanding stent 434 and helps to retain the stent on the outer surface of the inner member 410. The size of stent 434 varies, depending on the particular treatment and access site, as described above for balloon expanded stents.

A guide wire lumen 430 which preferably extends through the catheter is configured to receive guide wire 422. In order to implant self-expanding stent 434, guide wire 422 is positioned in a patient's body lumen, and typically guide wire 422 extends past a stenotic region. Distal end 408 is threaded over the proximal end of the guide wire which is outside the patient and catheter 400 is advanced along the guide wire until distal end 408 of catheter 400 is positioned within the stenosed region.

A stiffening mandrill may be incorporated in the proximal region of catheter 400 to enhance the pushability of the catheter through the patient's vascular system, and to improve the trackability of the catheter over the guide wire, as known in the art.

Preferably, Catheters 100, 400 may be used to implant the stent in a body lumen using an over-the-wire or rapid-exchange catheter configuration. Over-the-wire catheters are known in the art and details of the construction and use are set forth in U.S. Pat. Nos. 5,242,399, 4,468,224, and 4,545,390, which are herein incorporated by reference. Rapid-exchange catheters are also known in the art and details of the construction and use are set forth in U.S. Pat. Nos. 5,458,613; 5,346,505; and 5,300,085, which are incorporated herein by reference.

Catheter manufacturing techniques are generally known in the art. The disclosed catheter is preferably made in a conventional manner.

Stent

Figure 9:
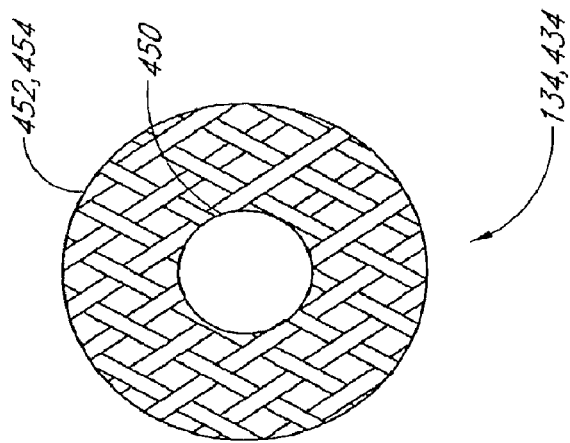
FIG. 9 is an end view of the stent of FIG. 7.
Figure 7:
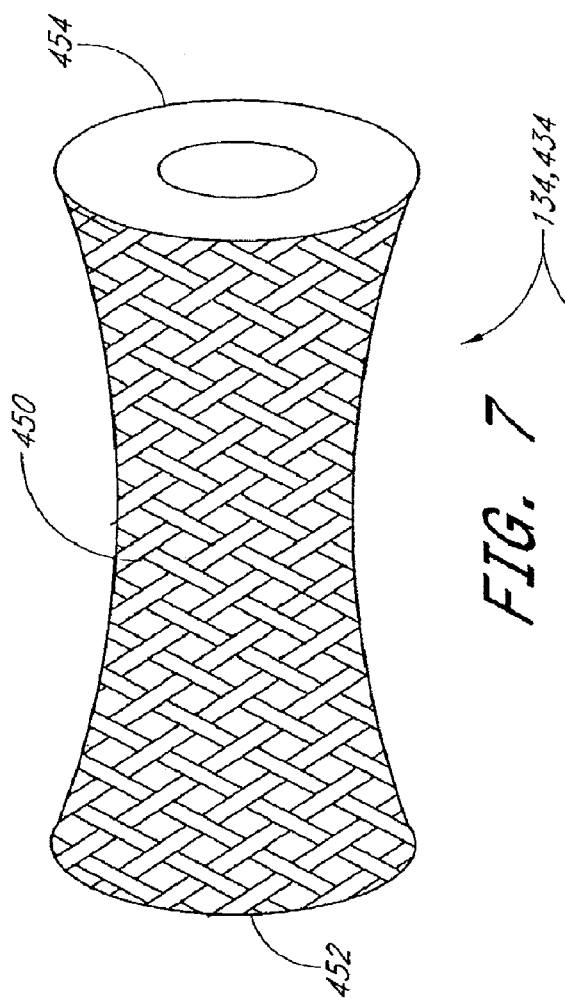
FIG. 7 is a perspective view of a stent in a deployed state in accordance with one embodiment.
Figure 8:
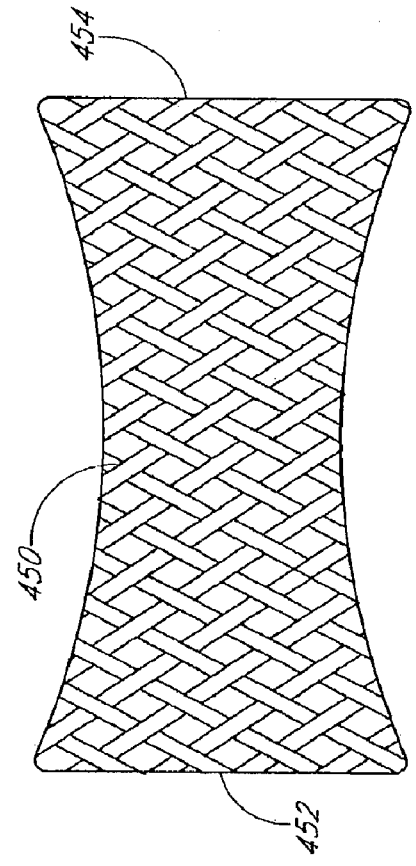
FIG. 8 is a side view of the stent of FIG. 7.

Stents 134 and 434 are shown in FIG. 7-9 in the expanded state. The stents 134, 434 have a center portion 450, a proximal end 452, and a distal end 454. The proximal end 452 and distal end 454 are curved outwards with respect to the center portion 450, as shown in FIGS. 7-9. Accordingly, the diameter at the proximal end 452 and distal end 454 are greater than the diameter at the center portion 450 when the stent is expanded. In some embodiments, the diameter at the proximal end 452 and distal end 454 are equal. In other embodiments, the diameter at the proximal end 452 is larger than the diameter at the distal end 454, or vice versa. The actual rate of taper between the proximal end 452, distal end 454 and center portion 450 may vary depending on the particular application.

FIG. 8A shows an alternative embodiment of a stent having the configuration shown in FIGS. 7-9. The stent 134, 434 of FIG. 8 may be a tubular member 456 having a porous structure or having holes 458. The tubular member 456 may be a graft material or other similar biocompatible materials.

Figure 10A:
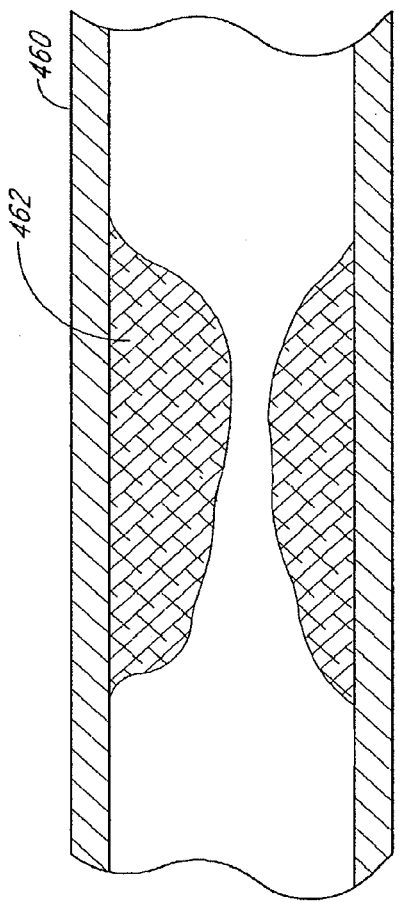
FIGS. 10A and B are schematic views of the stent being implanted in the body.
Figure 10B:
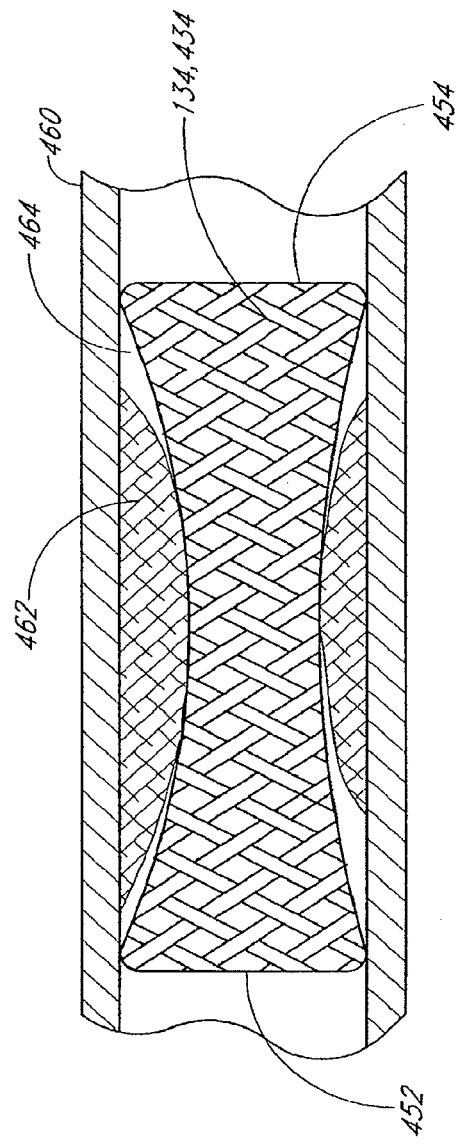
FIG. 10C is a schematic view of an alternative embodiment of an implanted stent.

FIG. 10A shows a body vessel 460 having a stenosis 462. FIG. 10B shows the stents 134, 434 implanted in the body vessel 460. The stent 134, 434 extends beyond the plaque or stenosis 462 to contain the stenosis between the proximal end 452 and distal end 454 of the stent. In one embodiment, a pocket 464 is left between the vessel 460 and stent 134, 434. In some embodiments, the stent 134, 434 extends about 1-6mm, and more preferably 3-5mm, beyond the plaque or stenosis 462 on each side of the stenosis, thereby containing growth and preventing spillover of the plaque. The actual dimensions of the stent and pocket may vary depending on the location of and degree of disease at the treatment site.

FIG. 10C shows the stent 134, 434 implanted in the body such that a pocket 464 is not left between the vessel 460 and stent 134, 434. Rather, the stent is expanded to conform to the stenosis. The configuration shown in FIG. 10C similarly contains growth and prevents spillover of plaque, by extending beyond the stenosis 462.

For the expandable stent 134, the balloon 114 is shaped such that it deploys in the configuration wherein the diameter at the proximal and distal ends 452, 454 are greater than the diameter at the center portion 450. For the self-expanding stent 434, the stent 434 is biased to expand in that same configuration. A number of different types of stents including balloon-expanding, self-expanding, tubular graft stents and any other type of stent that can take on the shapes depicted may be used.

Balloon-expanding stents such as the well-known Palmaz-Schatz balloon expandable stent, are designed to be expanded and deployed by expanding a balloon. Various kinds and types of stents are available in the market, and many different currently available stents are acceptable for use in the present invention, as well as new stents which may be developed in the future. The stent can be a cylindrical metal mesh stent having an initial crimped outer diameter, which may be forcibly expanded by the balloon to the deployed varied diameter. When deployed in a body passageway of a patient, the stent may be designed to preferably press radially outward to hold the passageway open.

Many balloon expandable stents are known in the art including plastic and metal stents, such as the stainless steel stent shown in U.S. Pat. No. 4,735,665; the wire stent shown in U.S. Pat. No. 4,950,227; another metal stent shown in European Patent Application EP0 707 837 A1 and that shown in U.S. Pat. Nos. 5,445,646, or 5,242,451, the disclosures of which are incorporated herein by reference.

Self-expanding stents such as that described in U.S. Pat. No. 4,655,771 to Wallsten, incorporated herein by reference, expand from a contracted condition where they are mounted on the catheter assembly, to an expanded condition where the stent comes in contact with the body lumen. The stents are self-expanding, which can be achieved by several means. The stents are preferably formed from a stainless steel material and are configured so that they are biased radially outwardly and expand outwardly unless restrained. The stents also can be formed from a heat sensitive material, such as nickel titanium, which will self-expand radially outwardly upon application of a transformation temperature. These stents are representative of a large number of stents which can be adapted to the configuration illustrated in FIG. 7-9.

Tubular graft stents include a tubular graft attached to a stent. The tubular graft may be a biocompatible porous or nonporous tubular structure to which a stent structure, such as a wire mesh, may be attached. The stent structure may be biased to assume an enlarged configuration corresponding to a target treatment site, but may be constrained in a contracted condition to facilitate introduction into a patient's vasculature. The tubular graft preferably a peripheral wall defining a periphery and a lumen therein, the lumen extending between the first and second ends of the tubular graft. The tubular graft may be provided from a polymeric material, such as polyester, polytetrafluorethaline, Dacron, Teflon, and polyurethane. The stent may be attached to the tubular graft by sutures, staples, wires, or an adhesive, or alternatively by thermal bonding, chemical bonding, and ultrasonic bonding. The stent is preferably formed from a metallic material, such as stainless steel or Nitinol, and may be a flat-coiled sheet with one or more serpentine elements formed therein, or a wire formed into a serpentine shape. The stent may be attached to an exterior surface of the tubular graft, to an interior surface of the tubular graft, or embedded in the wall of the tubular graft. The stent preferably is provided along the entire length of the graft. However, it is also envisioned that the stent may extend over a portion of the tubular graft. Alternatively, the graft may cover only a portion of the stent.

Configurations, such as helices, coils, braids, expandable tube stents, roving wire stents, and wire mesh stents or the like may be utilized with any of the above-described stents depending on the application for the device.

The stents as described herein can be formed from any number of materials, including metals, metal alloys and polymeric materials. Preferably, the stents are formed from metal alloys such as stainless steel, tantalum, or the so-called heat sensitive metal alloys such as nickel titanium (NiTi). The stent may be made of any suitable biocompatible material such as a metallic material or an alloy, examples of which include, but are not limited to, stainless steel, elastinite (Nitinol), tantalum, nickel-titanium alloy, platinum-iriidium alloy, gold, magnesium, or combinations thereof. Alloys of cobalt, nickel, chromium, and molybdenum may also be used. The stents may also be made from bioabsorbable or biostable polymers. Stents formed from stainless steel or similar alloys typically are designed, such as in a helical coil or the like, so that they are spring biased outwardly.

With respect to stents formed from shape-memory alloys such as NiTi, the stent will remain passive in its martensitic state when it is kept at a temperature below the transition temperature. In this case, the transition temperature will be below normal body temperature, or about 98.6° F. When the NiTi stent is exposed to normal body temperature, it will immediately attempt to return to its austenitic state, and will rapidly expand radially outwardly to achieve its preformed state. Details relating to the properties of devices made from nickel-titanium can be found in "Shape-Memory Alloys," Scientific American, Vol. 281, pages 74-82 (November, 1979), which is incorporated herein by reference.

The pattern of the stent can be cut from either a cylindrical tube of the stent material or from a flat piece of the stent material, which is then rolled and joined to form the stent. Methods of cutting the lattice pattern into the stent material include laser cutting and chemical etching, as described in U.S. Pat. No. 5,759,192 issued to Saunders and U.S. Pat. No. 5,421,955 issued to Lau, both patents incorporated herein by reference in their entirety. Alternative embodiments, as known to those of skill in the art, of manufacturing stents may also be used. The stents may also be polished, as known to those of skill of the art.

Furthermore, the stent can be coated with a drug or combination of drugs to prevent proliferation. In a preferred embodiment, the stents of the present invention are used to deliver more than one drug to a desired body location. Thus, treatment for different causes may be administered with a combination of drugs. In addition, more than one drug may be used for the same cause of restenosis, such that a reduced dosage may be administered, with lower risk of side-effects, and/or a more effective treatment of the cause. In addition, more than one drug may be administered for multiple causes of restenosis. Both long term therapies and short term therapies may be utilized. As used in this application, the term "drug" denotes any compound which has a desired pharmacological effect, or which is used for diagnostic purposes. Useful drugs include, but are not limited to angiogenic drugs, smooth muscle cell inhibitors, collagen inhibitors, vasodilators, anti-platelet substances, anti-thrombotic substances, anti-coagulants, gene therapies, cholesterol reducing agents and combinations thereof. The drugs may also include, but are not limited to anti-inflammatory, anti-proliferative, anti-allergic, calcium antagonists, thromboxane inhibitors, prostacyclin mimetics, platelet membrane receptor blockers, thrombin inhibitors and angiotensin converting enzyme inhibitors, antineoplastic, antimitotic, antifibrin, antibiotic, and antioxidant substances as well as combinations thereof, and the like.

Examples of these drugs include heparin, a heparin derivative or analog, heparin fragments, colchicine, agiotensin converting enzyme inhibitors, aspirin, goat-anti-rabbit PDGF antibody, terbinafine, trapidil, interferongamma, steroids, ionizing radiation, fusion tonixins, antisense oligonucleotides, gene vectors (and other gene therapies), rapamycin, cortisone, taxol, carbide, and any other such drug. Examples of such antineoplastics and/or antimitotics include paclitaxel, docetaxel, methotrexate, azathioprine, vincristine, vinblastine, fluorouracil, doxorubicin hydrochloride, and mitomycin. Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax. Examples of such cytostatic or antiproliferative agents include angiopeptin, angiotensin converting enzyme inhibitors such as captopril, cilazapril or lisinopril; calcium channel blockers (such as nifedipine), colchicine, fibroblast growth factor (FGF) antagonists, fish oil (omega 3-fatty acid), histamine antagonists, lovastatin (an inhibitor of antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax.

Examples of such cytostatic or antiproliferative agents include angiopeptin, angiotensin converting enzyme inhibitors such as captopril, cilazapril or lisinopril; calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug), monoclonal antibodies (such as those specific for Platelet-Derived Growth Factor (PDGF) receptors), nitroprusside, phosphodiesterase inhibitors, prostaglandin inhibitors, suramin, seratonin blockers, steroids, thioprotease inhibitors, triazolopyrimidine (a PDGF antagonist), and nitric oxide.

An example of an antiallergenic agent is permirolast potassium. Other therapeutic substances or agents that may be used include alpha-interferon, genetically engineered epithelial cells, and dexamethasone. In other examples, the therapeutic substance is a radioactive isotope for prosthesis usage in radiotherapeutic procedures. Examples of radioactive isotopes include, but are not limited to, phosphoric acid, palladium, cesium, and iodine. While the preventative and treatment properties of the foregoing therapeutic substances or agents are well-known to those of ordinary skill in the art, the substances or agents are provided by way of example and are not meant to be limiting. Other therapeutic substances are applicable.

The therapeutic agent may also be provided with a pharmaceutically acceptable carrier and, optionally, additional ingredients such as antioxidants, stabilizing agents, permeation enhancers, and the like. The drugs may also include radiochemicals to irradiate and/or prohibit tissue growth or to permit diagnostic imaging of a site.

Pits, pores, grooves, coatings, impregnateable materials, or a combination of these may be used to provide the drugs on the stent. In addition, a stent may include reservoirs or micropores to deliver drugs to the treatment site. Alternatively, the stent may include protruding structures which may have a central depression which may contain a therapeutic substance. Protruding structures are disclosed in U.S. Pat. No. 6,254,632, the disclosure of which is hereby incorporated by reference. These pits, pores, grooves, reservoirs, and protruding structures may be of any shape and size which may permit adequate drug delivery to the treatment site.

In an alternative embodiment, the stent may comprise a plurality of microencapsulated spheres containing a medicament, the microencapsulated spheres being disposed about the exterior surface of the stent so as to rupture upon radial expansion of the stent by a predetermined amount. The microencapsulated spheres are preferably encapsulated in a coating applied to the exterior surface of the stent. The spheres are preferably made from a bioabsorbable or biostable material.

In yet another embodiment, the stent may be coated with or have as part of construction a collagen sponge (and possibly associated anchor material). Collagen sponges, and associate anchor materials, are known for use with other treatment modalities, such as to close wounds. In this embodiment, the collagen sponge carries the therapeutic agent, and releases the agent slowly over a period of days. Release of agents over 30-90 days may be beneficial. For example, Cyclosporins are now used in stents, but the agent is depleted in about 60 days. By using a collagen sponge as a coating or part of the stent, the Cyclosporin may continue to be delivered by the sponge for more than 60 days. This minimizes tissue reaction.

In one embodiment, the therapeutic agent may be located only on the outer surface of the stent, such that the stenosis 460 is exposed to the therapeutic agent (see FIG. 10B). By limiting the regions which are exposed to the therapeutic agent to the affected vessel site, side effects commonly associated with drug treatments may be reduced. Furthermore, the stent may include a therapeutic agent or combination of therapeutic agents which can provide for long-term drug delivery at the vessel site.

Although a number of methods for applying drugs to a stent have been discussed, additional methods of incorporating drugs with a stent are known in the art and may be used.

Directional Catheter

Often vessels are injured while the guidewire is manually manipulated. In particular, doctors often have a difficult time manipulating a guidewire into a smaller or tortuous branch of a bifurcated vessel. Accordingly, a device is needed which protects the vessel and guides the guidewire into smaller vessels without further injuring the patient.

Figure 11:
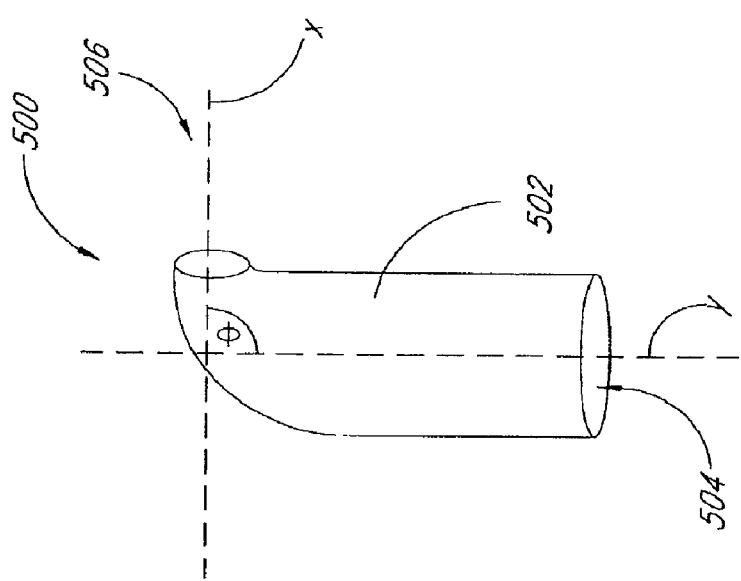
FIG. 11 is a perspective view of a directional catheter in accordance with one embodiment.

In accordance with another embodiment, a directional guide catheter 500 is provided for use with a guidewire delivery system, as shown in FIG. 11. The directional guide catheter 500 includes a tubular body 502 having a proximal end 504 and a distal end 506. The tubular body 502 preferably has an outer radius forming an outer bend 508, such that an axis x passing through the proximal end 504 and an axis y passing through the distal end 506 are arranged at an angle θ, corresponding to the angle between the bifurcated vessels. The directional catheter 500 can come in a variety of different sizes, in accordance with the various vessels in the body. The diameters of the tubular body 502 at the proximal end 504 and the distal end 506 may vary. The diameter at the distal end 506 may be the same size as the smaller portion of the bifurcated vessel. The diameter at the proximal end 504 may be substantially the same size as the larger portion of the bifurcated vessel. Alternatively, the diameter at the proximal end 504 and the diameter at the distal end 506 may be the same size.

The tubular body of the directional catheter is preferably extruded. The tubular body is preferably made of a polymer such as Nylon, the stiffness of which may be selected as appropriate. Material selection varies based on the desired characteristics.

Figure 12:
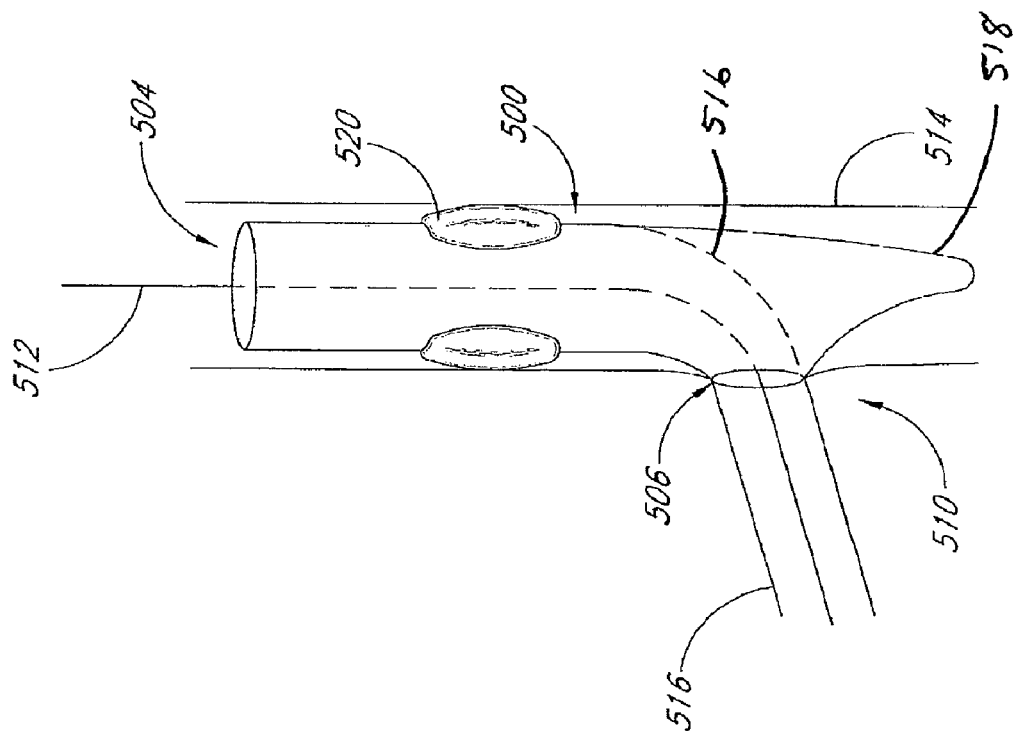
FIG. 12 is a schematic view of the directional catheter in the body.

In use, the directional guide catheter 500 is delivered to a bifurcation site 510, as shown in FIG. 12. The directional guide catheter 500 may initially slide over a guidewire 512, and then directs the guidewire 512 from a larger vessel 514 to a smaller vessel 516. The directional guide catheter 500 lines the guidewire up so that it can easily access the smaller vessel 516 without injuring the vessels at the bifurcation site 510. As shown in FIG. 12, the diameter at the distal end 506 of the tubular body 502 is substantially the same dimensions as the smaller vessel 516. Similarly, the proximal end 504 of the tubular body 502 is substantially the same dimensions as the larger vessel 514.

The directional guide catheter 500 may include a balloon 520 to secure and stabilize the directional guide catheter 500 at the bifurcation site 510. The directional guide catheter 500 and balloon 520 preferably permit the blood supply to continue through perfusion techniques as known in the art. The directional catheter 500 may be removed once the guidewire is positioned, before additional procedures are performed.

Advantageously, the curved portion 516 of the directional guide catheter 500 is constructed of a slightly higher durometer materials, so that the guidewire 512 is more easily directed along the curve. In addition, preferably, a guiding tip 518, is configured of radiopaque material in order to be property viewed for location in the artery.

Atherectomy Device

Figure 13:
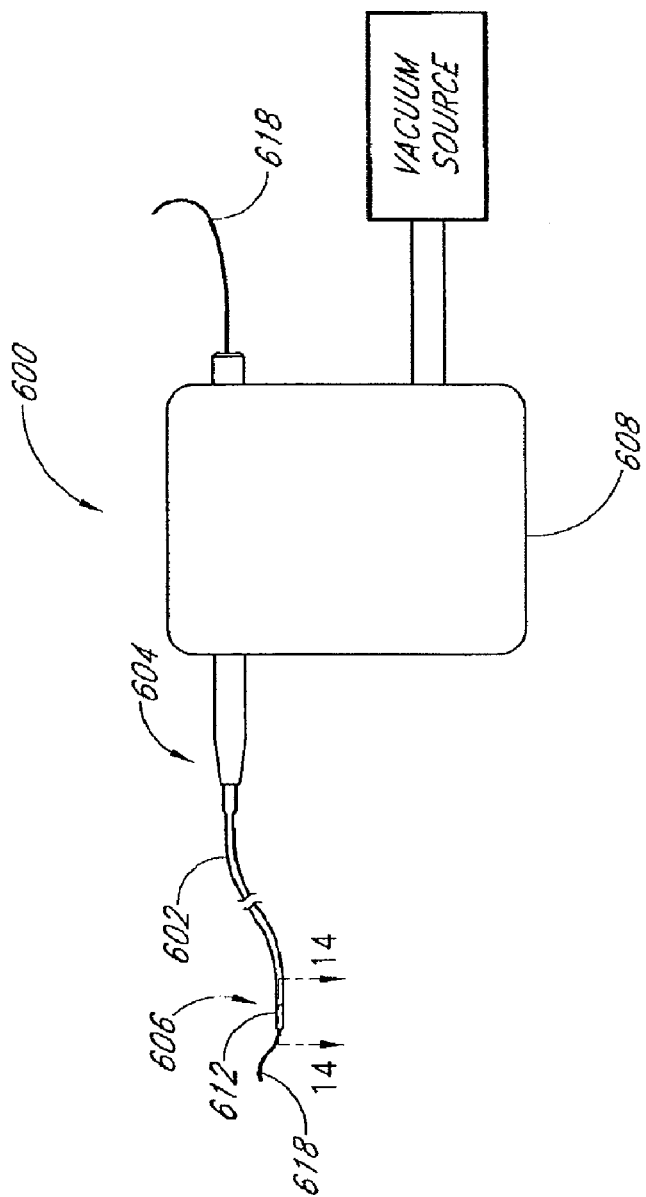
FIG. 13 is a perspective view of an atherectomy device in accordance with one embodiment.

In accordance with another embodiment, an improved atherectomy device is shown in FIG. 13. In some embodiments, the diseased vessel portions and/or plaque may be cut out prior to implanting a stent at the site, thereby preventing or reducing a restenosis. Current atherectomy devices are known to often damage non-diseased vessel portions. An atherectomy device having a cutting element and protective housing is disclosed. The housing is a shield for protecting the non-diseased vessel portions, but the cutter is extendable from the housing for treatment.

With reference to FIG. 13, atherectomy device 600 includes an elongate flexible tubular body 602 having a proximal end 604 and a distal end 606. A control 608 is preferably provided at or near the proximal end 604 of the tubular body 602 for permitting manipulation of the atherectomy device 600.

The tubular body 602 preferably has an elongate central lumen. An axially movable flexible drive shaft 608 is provided within central lumen. In some embodiments, the tubular body 602 may also contain a lumen for slideably receiving a guidewire, over which the atherectomy device 600 may slide to access a body site.

The atherectomy end 650 of the atherectomy device 600 is shown in more detail in FIG. 14. A cylindrical sleeve 612 having a central lumen 614 surrounds a cutting element 610. The flexible drive shaft 608 is attached to the cutting element 610. The cylindrical sleeve 612 is attached to tubular body 602. The cutting element 610 can have any configuration as known to those of skill in the art. In some embodiments, the cutting element 610 can include a plurality of blades 611. The atherectomy device 600 may include a vacuum (FIG. 13) to collect the material cut by the cutting element 600.

The cutting element 610 is axially movable such that the cutting element is within the sleeve 612 during delivery to the vessel site, and can be distally extended outside of the sleeve 612 at the vessel site. Accordingly, intermediary vessels are not harmed in delivery of the atherectomy device 600 to the vessel site.

It is also envisioned that the atherectomy device 600 can be arranged such that the tubular body 602 and cutting sleeve 612 are axially movable, such that the tubular body and cutting sleeve 612 are proximally retracted to expose cutting element 610.

In one embodiment, as shown in FIG. 13, the tubular body 602 may be provided with a central lumen (not shown) for slidably receiving a guidewire 618 to guide the atherectomy device 600 to the vessel site. The cutting element 610 may also include a central lumen (not shown) in such a configuration.

Figure 16A:
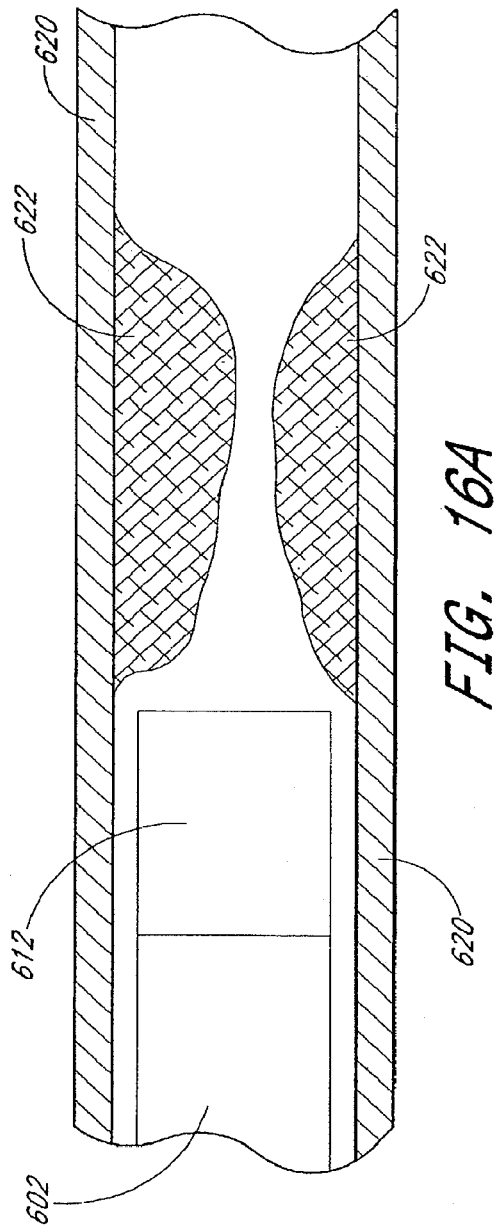
FIGS. 16A and B are schematic views of the atherectomy device of FIG. 13.
Figure 16B:
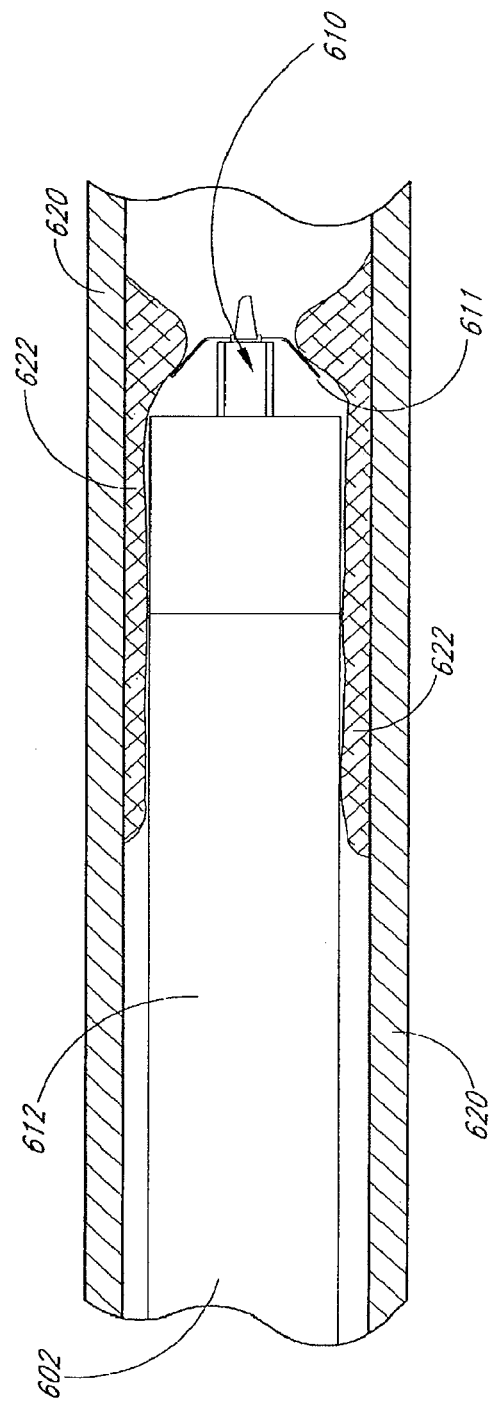
FIGS. 16C and D are schematic views of an alternative embodiment of the atherectomy device.

A method of using the atherectomy device 600 is illustrated in FIGS. 16A and 16B. FIG. 16A shows the atherectomy end having a tubular body 602 and cutting sleeve 612 being delivered to a vessel 620 having a stenosis 622. FIG. 16B shows the cutting element 610 extending distally from the cutting sleeve 612 to cut and remove the stenosis 622. In some embodiments, the entire diseased portion of the vessel may be removed. In other embodiments, only the stenosis 622 or a portion of the stenosis 622 is removed. The vacuum may be used to extract the debris from the treatment site before removal of the atherectomy device.

Figure 16C:
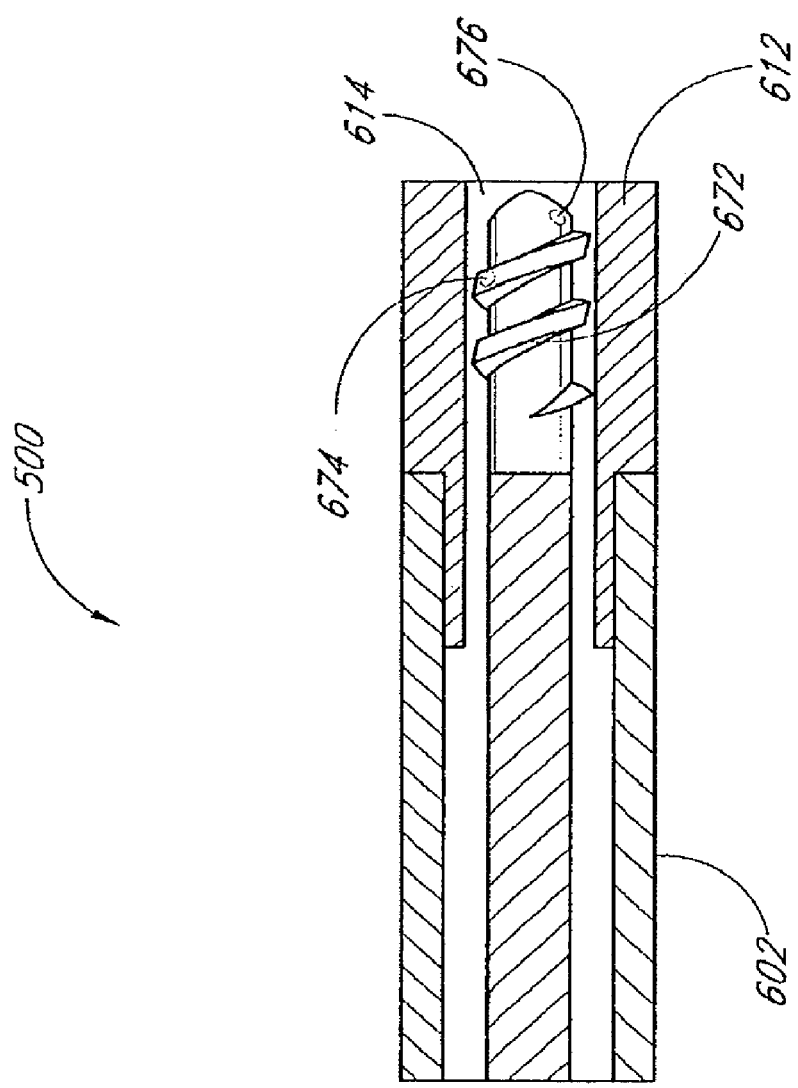
Figure 16D:
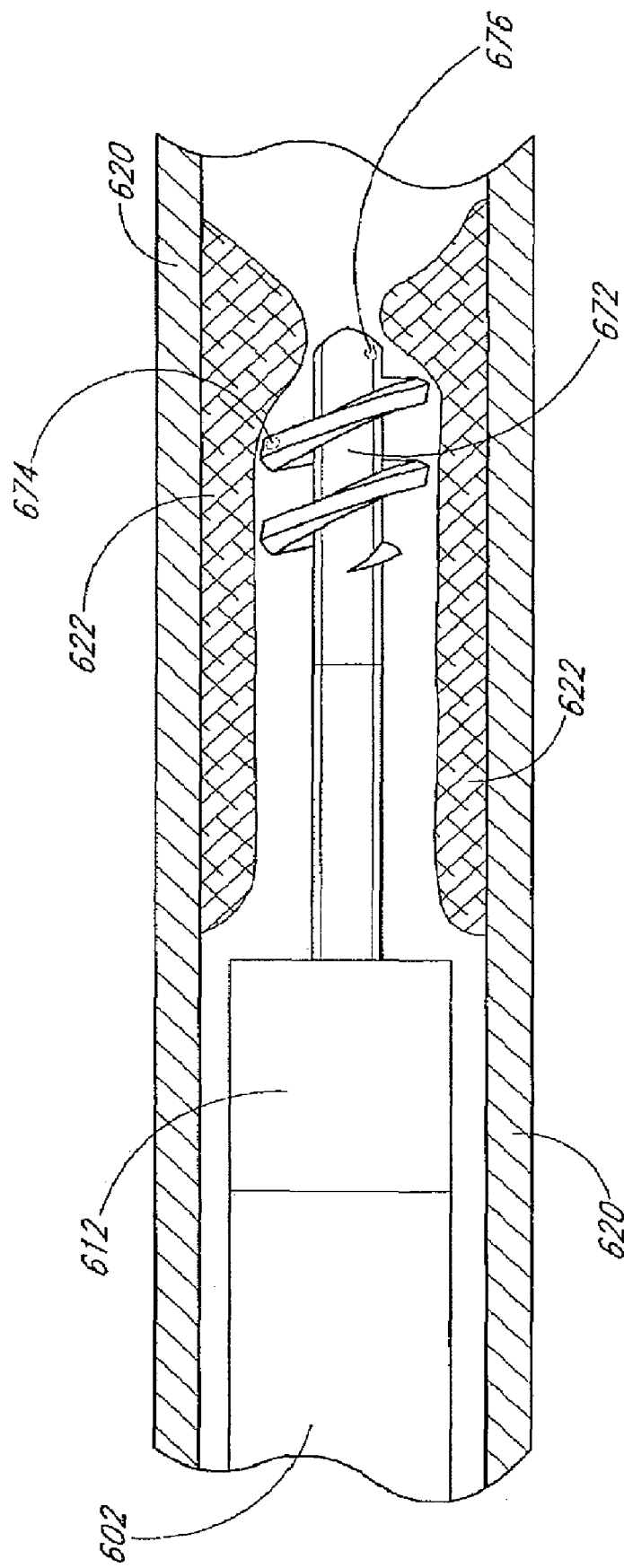

In another embodiment, the motive force for the blade may be provided by the vacuum and/or an irrigation port. An example of an alternative embodiment where such a propulsion system may be provided is depicted in FIGS. 16C and 16D. An atherectomy end 670 has a drill bit style cutter 672. Advantageously, this cutter has influent port 674 advantageously coupled to the vacuum and/or effluent port 676 for irrigation. The effluent port 676 is coupled to an irrigation lumen. The influent port 674 may advantageously be moved proximally or distally on the cutter 672 during manufacturing for optimization for different types of debris removal. Advantageously, either or both of the ports 674, 676 could provide propulsion by providing a directional jet or suction port.

Re-Impregnation Catheter

Figure 17A:
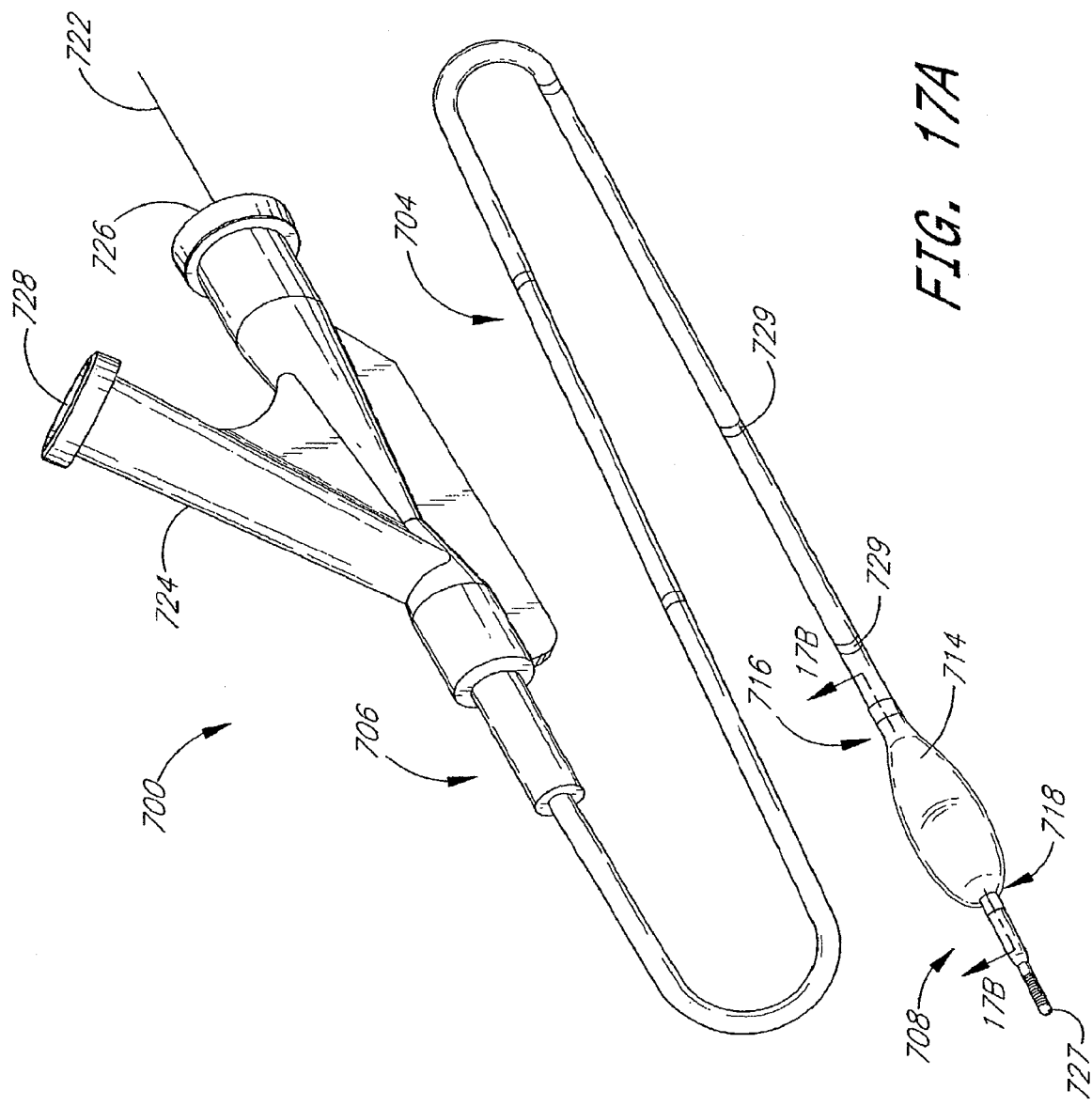
FIG. 17A is a perspective view showing a catheter having a balloon in accordance with an embodiment.
Figure 17C:
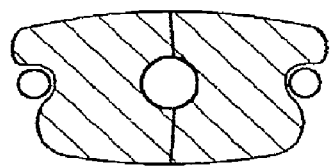
FIG. 17C is a detailed cross-sectional view of the distal end of the catheter and balloon of FIG. 17B through line 17C-17C.
Figure 17B:
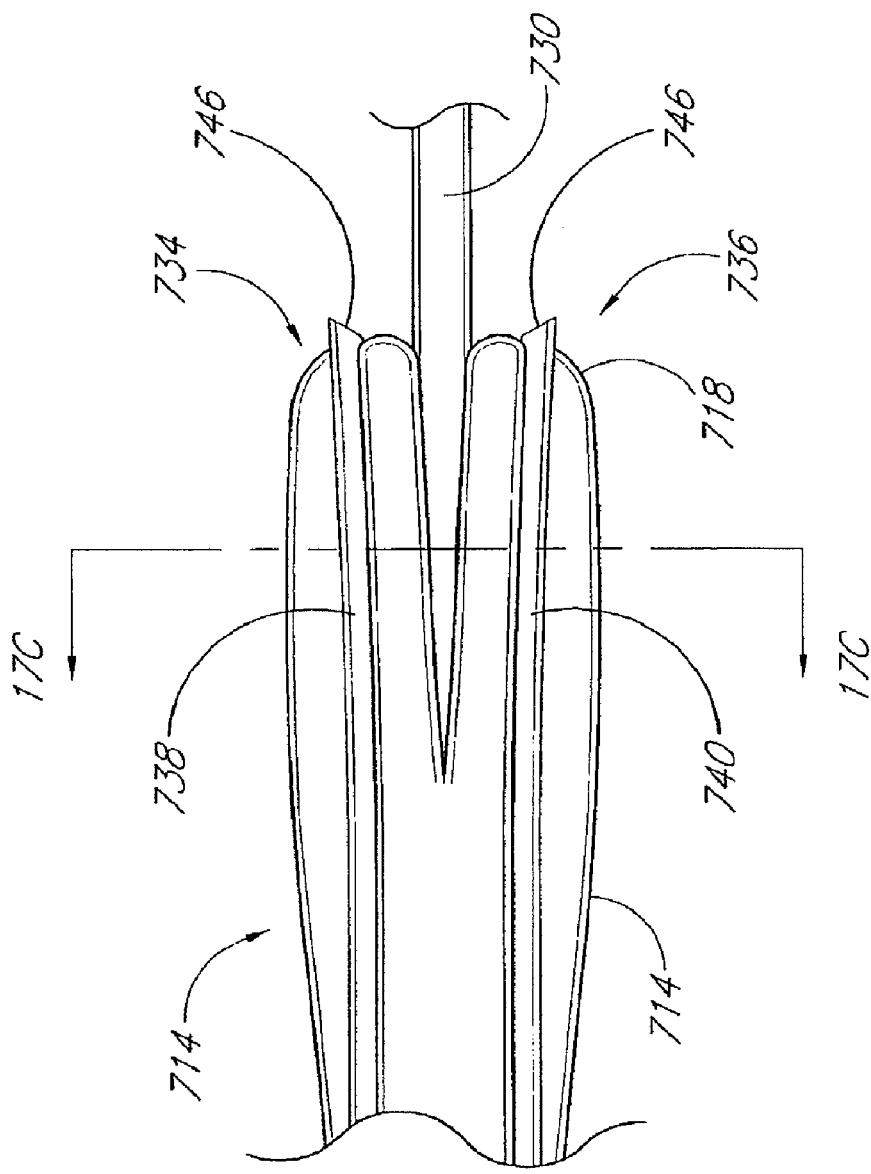
FIG. 17B is a detailed magnified view of the distal end of the catheter and balloon of FIG. 17A through line 17B-17B.

A method of re-impregnating, administering a drug on a deployed stent, or delivering an agent to a lesion or stenosis is also provided. A drug delivery catheter 700 is shown in FIGS. 17A and 17B. Delivery catheter 700 preferably includes an elongate, flexible tubular shaft 704, having a proximal end 706 and a distal end 708. The shaft 704 defines one or more passages or lumens extending through the shaft.

Catheter 700 preferably comprises a balloon 714, having a proximal end 716 and a distal end 718. Elongate shaft 704 preferably includes a guide wire 722, extending from distal end 716 through proximal end 706 of shaft 704, providing rigidity to device 700. Catheter 700 also includes a manifold 724. Manifold 724 preferably includes a guide wire port 726 and an inflation port 728. Catheter 700 may also include radiopaque markers 729 to view the location of catheter 700 within the patient's body lumen. Catheter 700 may also include a soft, flexible distal tip 727. Such catheters are known.

FIG. 17B illustrates a view of the magnified distal end 718 of the balloon 714. A guide wire lumen 730 is depicted. The guide wire lumen 730 is adapted to receive an elongate guide wire in a sliding fashion through proximal guide wire port 726 (FIG. 17A) in catheter manifold 724.

Preferably, an inflation lumen is connected to the balloon 714 to selectively inflate it with the inflating fluid. The inflation lumen provides fluid communication between the interior of the balloon 714 and the inflation port 728 located at manifold 724. The inflation lumen may also be adapted to hook up to a vacuum, to eliminate air bubbles. Alternatively, a separate lumen may be provided for connection with the vacuum.

The catheter shaft 704 may have various configurations other than the coaxial design shown in the drawings, including a single extruded multi-lumen tube defining any suitable number of colinear or radially aligned lumens.

The balloon 714 may comprise any known balloon configurations.

In one embodiment, the balloon 714 includes a first balloon element 734 and a second element 736, each having an associated needle element 738 and 740, respectively. The needle elements 738 and 740 have a pointed end 746 and include an inner lumen, which is used to deliver at least one therapeutic agent. Any therapeutic agent, such as those discussed above, may be used. The pointed ends 746 may be used to cut into bodily tissue or to contact an indwelling stent. When the balloon is expanded, the needle elements 738 and 740 are pushed outwardly. The needles can be advanced distally to impregnate an already deployed stent or medicate bodily tissue with the at least one therapeutic agent upon balloon expansion and contact with the stent or bodily tissue.

The catheter manifold 724 provides a maneuvering handle for the health care professional, as well as an inflation port 728 and a guide wire port 726. Either or both the inflation port 728 or the guide wire port 726 may have a coupling, accompanied by a luer-lock fitting for connecting an inflation lumen to a source of pressurized fluid in a conventional manner. The manifold 724 may also include an injection port for allowing radiopaque contrast fluid to be injected through the outer sleeve and around the catheter shaft, thus illuminating the delivery device on a fluoroscope. The proximal manifold 724 is preferably injection molded of any suitable material. A precision gasket may also be provided, which seals securely around the device, prohibiting fluid loss. Many other catheter configurations are also known.

The size of balloon 714 varies, depending on the particular treatment and access site. The overall length and diameter may vary based on the treatment. In a preferred embodiment, balloon 714 has an inflated length between about 1 and 10 cm, preferably about 4 cm. In a preferred embodiment, balloon 714 has an inflated diameter between about 0.1 and 1.5 cm. However, balloons of any dimensions may be used.

Catheter manufacturing techniques are generally known in the art, including extrusion and coextrusion, coating, adhesives, and molding. The disclosed catheter is preferably made in a conventional manner. The elongate shaft of the catheter is preferably extruded. The elongate shaft is preferably made of a polymer such as Nylon, the stiffness of which may be selected as appropriate. Material selection varies based on the desired characteristics. The joints are preferably bonded. Biocompatible adhesives are preferably used to bond the joints. The balloon is also preferably made in a conventional manner. However, other configurations are also acceptable.

Figure 18A:
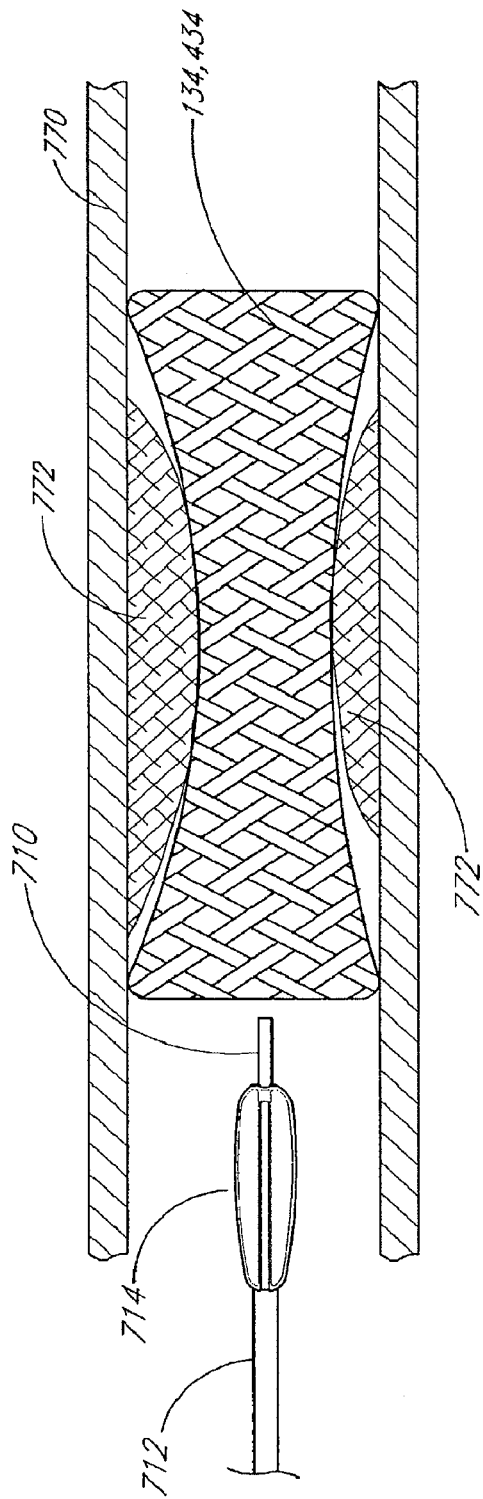
FIGS. 18A and B are schematic views of the catheter of FIGS. 17A-17B in use in the body.
Figure 18B:
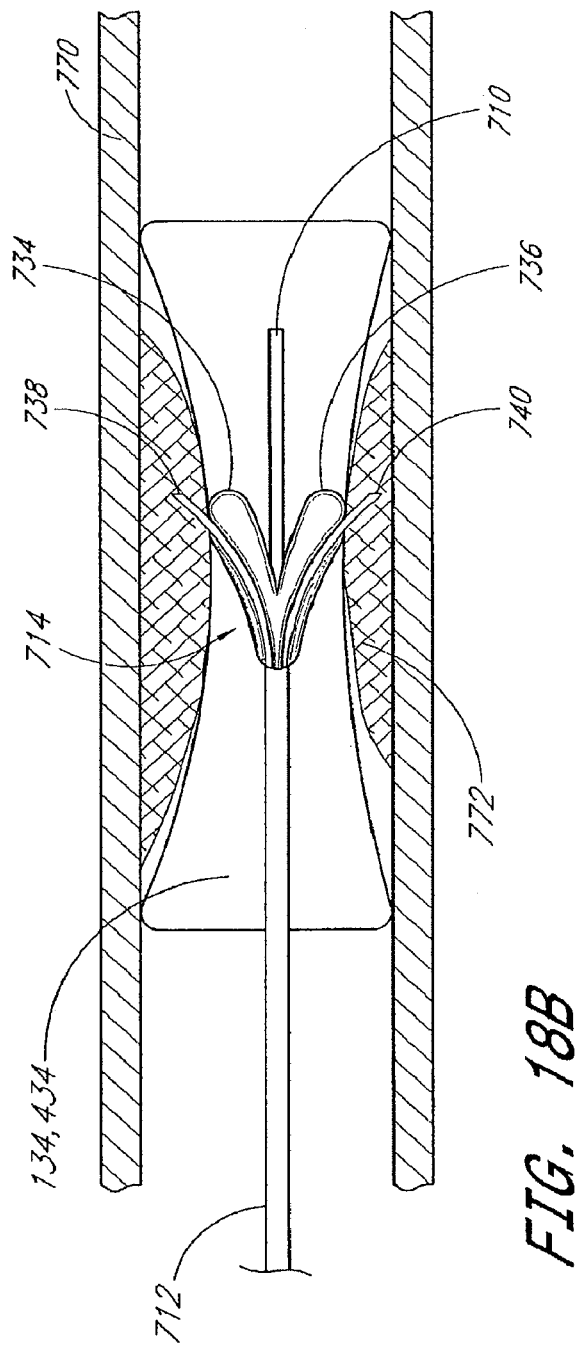
FIG. 18C is a schematic view of an alternative embodiment of the catheter depicted in FIGS. 17 and 18.

As shown in FIGS. 18A and 18B, the drug delivery catheter 700 is shown in use. FIG. 18A shows a body vessel 770 having a stenosis 772, and a stent 134, 434 deployed within the body vessel 770. The impregnation catheter 700 is shown in the body vessel. FIG. 18B shows the drug impregnation catheter medicating the stenotic region in the body vessel 770. The balloon 714 is expanded, such that balloon element 734 and balloon element 736 contact different portions of the stent 134, 434. The needle elements 738 and 740 bear upward via the balloon elements 734 and 736 into the stenosis 772. A treatment agent is delivered to the stenosis 772 through the needle elements 738 and 740.

Figure 18C:
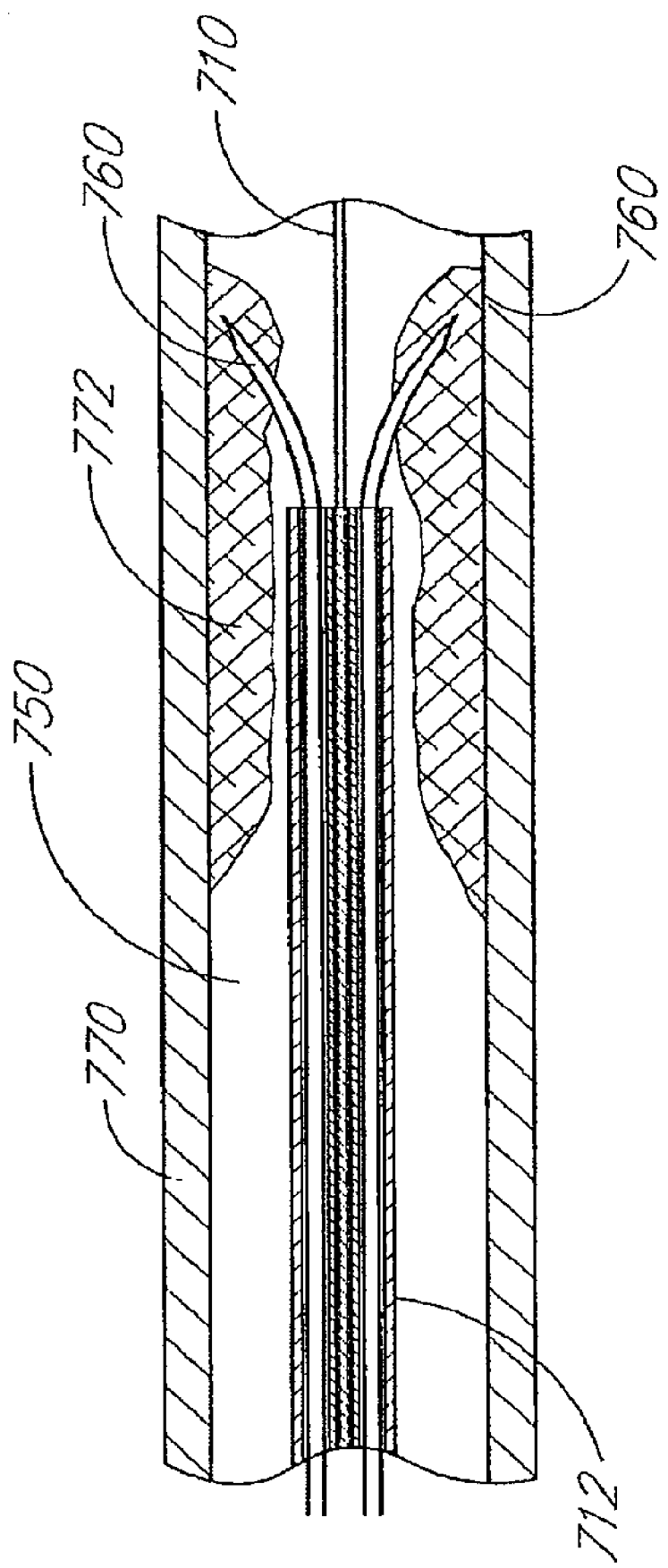

FIG. 18C depicts an alternative embodiment of the drug delivery catheter. In this embodiment, needle elements 760 are pre-biased outward. They are maintained in a sheath 712 until they are advanced to the lesion 772. Then the needle elements 760 are advanced out of the sheath 712, and due to the bias, can enter or bear on the lesion 772. The needles may also deliver radiopaque material.

Improved Lesion Mapping

In a further embodiment, the catheter 700 of FIG. 17A does not carry needles, but is provided for better mapping of vascular lesions. Preferably, the balloon is made of a very thin membrane. The balloon 714 membrane would be thin enough that when gently inflated, in a lesion, it conforms to the lesion topography. The inflation medium is radiopaque, so that with the balloon 714 inflated, the precise contours of the lesion would be visible on X-ray. This embodiment provides an improvement over conventional angiograms, where the radiopaque dies flows through the arteries, and the mapping is imprecise. The balloon 714, when embodied in this fashion, is inflated slowly and at low pressure, just to bear on the lesion and conform to the lesion for mapping through radiopaque techniques. Advantageously, the catheter also permits blood flow past the balloon during the procedure using constructions that provide such blood flow as are known in the art, such as in U.S. Pat. No. 4,581,017. In addition to improved mapping, such a balloon is advantageous for angioplasty procedures of small or tortuous vessels, where conventional, relatively stiff catheters cannot be manipulated.

Method

With reference to FIGS. 19-24, one method of inhibiting restenosis in accordance with the present invention is shown.

In accordance with one embodiment a method of delivering a stent of the present invention is shown. As previously discussed self-expanding and balloon expanding stents may be used. A delivery system for balloon expanding stents, and a delivery system for self-expanding stents have also been described herein. Tubular graft stents may be used with either self-expanding or balloon-expanding systems.

In either system, the delivery system is preferably percutaneously delivered to the treatment site. The stent is percutaneously introduced in the contracted condition, advanced to a treatment site within a body vessel, and deployed to assume an enlarged condition and repair and/or bypass the treatment site.

A method of delivering a stent system as described above generally includes locating the site to be treated, providing a suitable delivery catheter, positioning the distal portion of a delivery catheter with a stent disposed thereon or therein in the branch of the site to be treated, partially deploying the stent in a vessel, adjusting the position of the stent if necessary, and then fully deploying the stent. Methods of navigating catheters through blood vessels or other fluid conduits within the human body are well known, and will therefore not be discussed herein.

In order to visualize the position of a partially or fully-deployed stent with a suitable radiographic apparatus, a contrast media may be introduced through the catheter to the region of the stent placement. Many suitable contrast media are known to those skilled in the art. The contrast media may be introduced at any stage of the deployment of the stent system. For example, a contrast media may be introduced after partially deploying the stent, or after fully deploying the stent.

Figure 21:
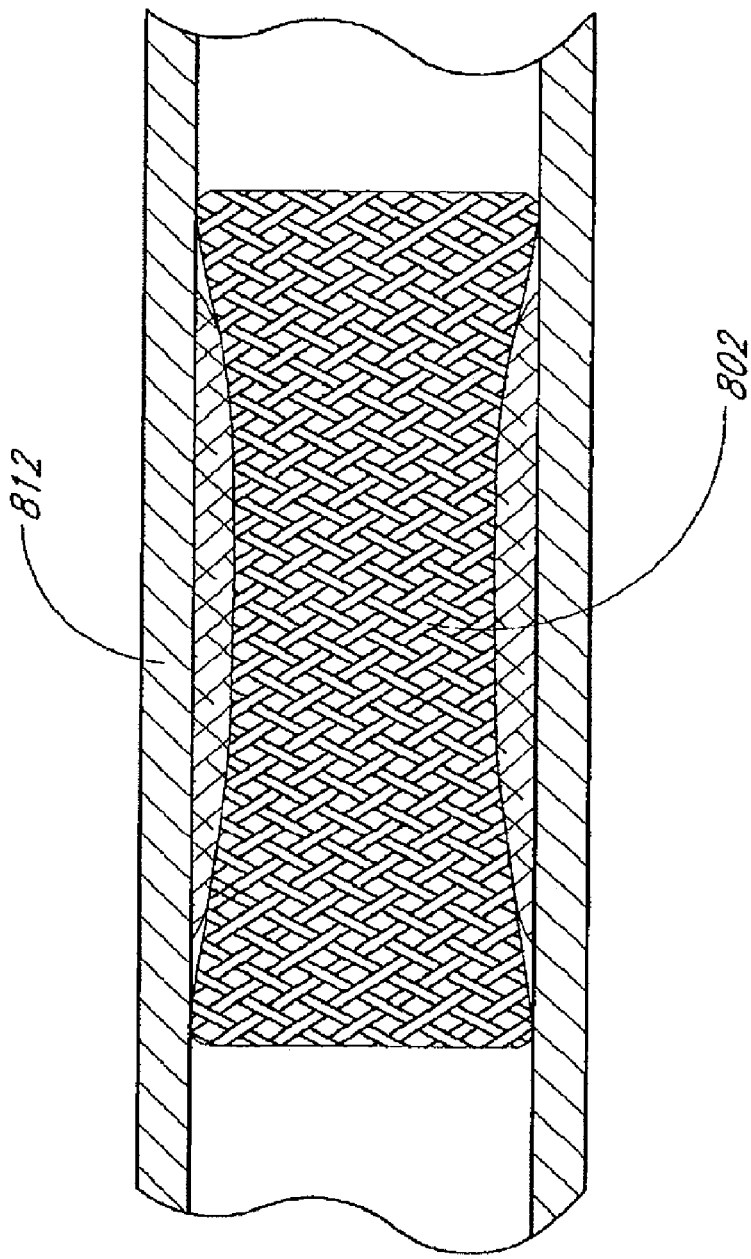

With respect to the balloon expanding delivery system 800 as shown in FIGS. 19-21, a method frequently described for delivering a stent to a desired intraluminal location includes mounting the expandable stent 802 on an expandable member 804, such as a balloon, provided on the distal end 806 of a catheter 808, advancing the catheter to the desired location 810 within the patient's body lumen 812 (FIG. 19), inflating the balloon 804 (FIG. 20) on the catheter 800 to expand the stent 802 into a permanent expanded condition and then deflating the balloon 804 and removing the catheter 800. When fully deployed and implanted, as shown in FIG. 21, stent 802 will support and hold open stenosed region 810 so that blood flow is not restricted.

Figure 22:
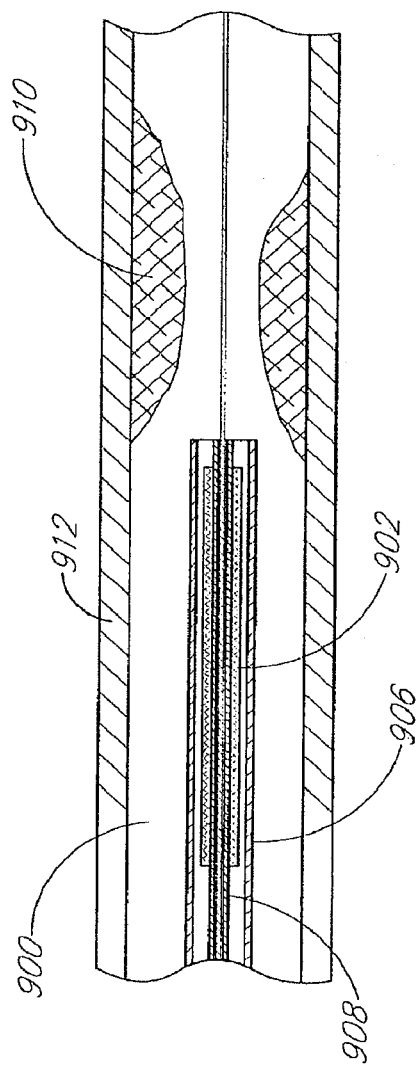
Figure 23:
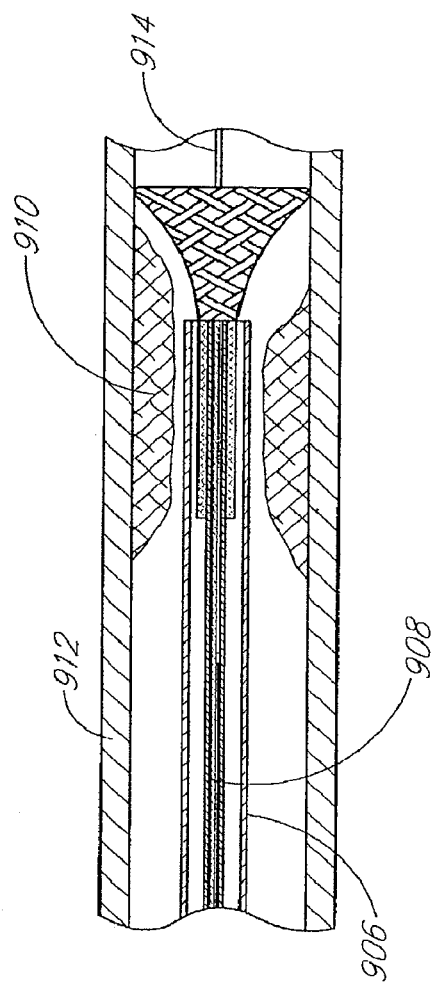
Figure 24:
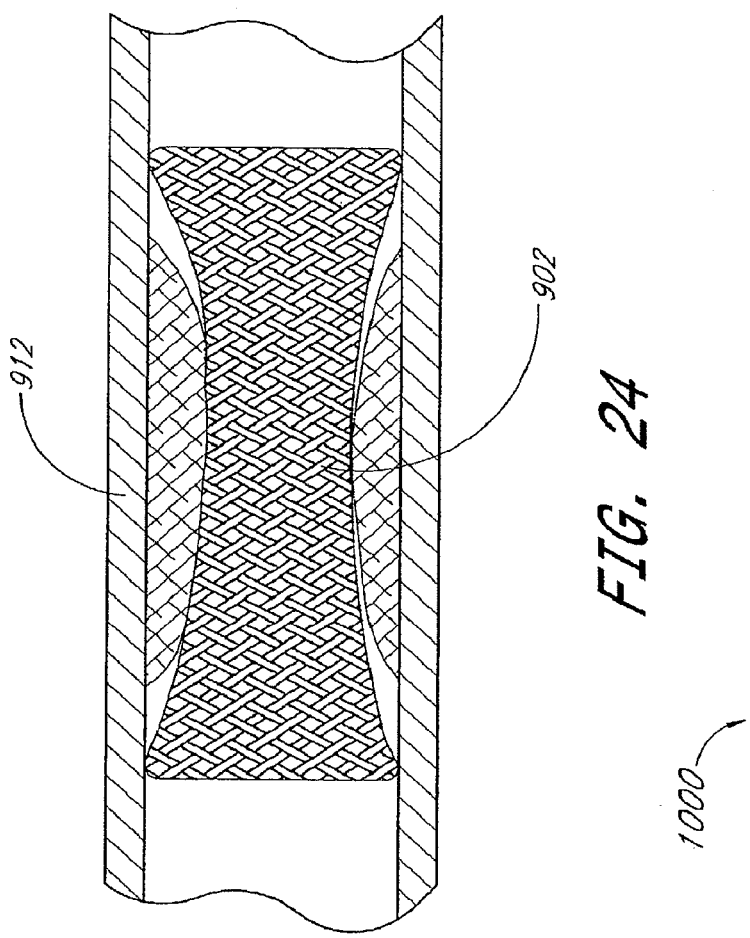

With respect to the self-expanding delivery system 900 as shown in FIGS. 22-24, self-expanding stent 902 is implanted in stenosed region 910 by moving outer member 906 in a proximal direction while simultaneously moving inner member 908 in a distal direction (FIG. 22). With reference to FIG. 23, as portions of self-expanding stent 902 are no longer contained by outer member 906, it will expand radially outwardly into contact with vessel wall 912 in the area of stenosed region 910. When fully deployed and implanted, as shown in FIG. 24, stent 902 will support and hold open stenosed region 910 so that blood flow is not restricted.

In accordance with another aspect of the present invention, atherectomy may be performed at the treatment site prior to stent delivery. The atherectomy may be performed using known chemical atherectomy solutions. Alternatively, the atherectomy may be performed using an atherectomy device. Preferably, the atherectomy device includes a protective housing member, as described above with reference to FIGS. 13-16, to prevent injury to non-diseased vessels, but can be extended from the housing for treatment.

In accordance with another aspect of the present invention, a stent may be impregnated with a therapeutic agent after stent deployment. As described above with reference to FIGS. 17-18, a catheter having a balloon mounted at its distal end may be delivered to a treatment area having a deployed stent. The balloon comprises needle elements including at least one therapeutic agent, which impregnate into a stent or bodily tissue when the balloon is expanded, contacts the stent, and the needle elements are deployed.

In accordance with another aspect of the present invention, a directional catheter may be used to access the treatment site via guidewire. As described above with reference to FIGS. 11 and 12, the directional catheter is delivered to a bifurcated vessel to guide the guidewire to a smaller branch of the vessel, thereby reducing injury to the vessels.

Figure 25:
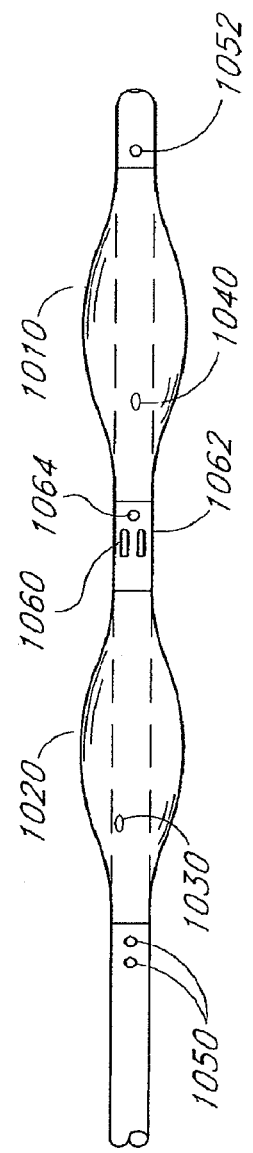
FIG. 25 depicts a multi-balloon inspection catheter.

FIG. 25 illustrates a multi-balloon catheter 1000 design for inspection or treatment of body lumen. The catheter has two balloons 1010, 1020, in this embodiment. Each is inflatable through an inflation port 1030, 1040 that provides fluid communication to an inflation lumen in the catheter shaft. Preferably, this catheter also permits blood flow past the balloons, in a manner known in the art. For this purpose, influent perfusion ports 1050 and effluent perfusion ports 1052 are provided. Between the balloons is positioned a camera or lens 1060 for observation and inspection of a lumen. This lens 1060 may be coupled to a fiber optic to transmit the optical properties to a camera at the proximal end of the catheter 1000, or it may be a CCD viewer or the like to provide electrical signals with an image. The catheter 1000 may also include an ultrasound device 1062, such as an intravascular ultrasound (IVUS). Preferably, also positioned between the balloons are one or more fluid ports 1064. Advantageously a suction port 1064 and an infusion port (not shown) are provided. These ports permit removal of blood between the balloons, and infusion with a more transparent medium, through which optical images may be made. Alternatively, a radiopaque material may be infused and held in the regions between the balloons, with the lumen sealed by the balloons, so as to obtain more precise mapping through radiographic techniques.

The foregoing description details certain embodiments of the inventions. It will be appreciated, however, that no matter how detailed the foregoing appears in text, the inventions can be practiced in many ways. As is also stated above, it should be noted that the use of particular terminology when describing certain features or aspects of the inventions should not be taken to imply that the terminology is being re-defined herein to be restricted to including any specific characteristics of the features or aspects of the invention with which that terminology is associated. The scope of the invention should therefore be construed in accordance with the ordinary and customary meaning of the appended claims and any equivalents thereof.

What is claimed is:

1. A method of mapping a vascular lesion comprising:
   delivering a thin membrane balloon comprised of a radiopaque material to the vascular lesion; and
   inflating the balloon such that the balloon conforms to a topography of the lesion for mapping the lesion, wherein inflating the balloon comprises inflating at a low pressure.

2. A lesion mapping catheter comprising:
   an elongate tubular shaft having a proximal end and a distal end;
   a thin membrane balloon comprised of a radiopaque material, the balloon positioned inside the tubular shaft;
   wherein the balloon is configured such that when inflated inside a vascular lesion the membrane conforms to a topography of the vascular lesions, wherein the balloon is configured to be inflated at a low pressure.

* * * * *

UNITED STATES PATENT AND TRADEMARK OFFICE
CERTIFICATE OF CORRECTION

PATENT NO.         : 7,468,052 B2
APPLICATION NO. : 11/757960
DATED                : December 23, 2008
INVENTOR(S)      : Balbir S. Brar and Harvinder Sahota It is certified that error appears in the above-identified patent and that said Letters Patent is hereby corrected as shown below:

At Column 1, line 3, below Title, please insert heading --Cross-Reference to Related Applications--.

At Column 1, line 4, after "2003" insert --now Pat. No. 7,226,473--.

At Column 5, lines 48-49, change "self-explanding" to --self-expanding--.

At Column 6, line 38, change "FIG. 7-9" to --FIGS. 7-9--.

At Column 7, line 48, change "FIG. 7-9" to --FIGS. 7-9--.

At Column 7, line 60, change "polytetrafluorethaline" to --polytetrafluoroethylene--.

At Column 8, line 18, change "elastinite" to --elasticite--.

At Column 9, line 9, change "agiotensin" to --angiotensin--.

At Column 9, line 12, change "tonixins," to --toxins,--.

At Column 9, line 48, change "serotonin" to --serotonin--.

At Column 9, line 51, change "permirolast" to --pemirolast--.

At Column 10, line 3, change "impregnateable" to --impregnatable--.

At Column 12, line 42, change "Re-Impregnation" to --Re-impregnation--.

Signed and Sealed this

Eleventh Day of August, 2009

David J. Kappos
*Director of the United States Patent and Trademark Office*